United States Patent [19]
Kaltenbach et al.

[11] Patent Number: 5,804,022
[45] Date of Patent: Sep. 8, 1998

[54] METHOD FOR MAKING MINIATURIZED PLANAR COLUMNS IN NOVEL SUPPORT MEDIA FOR LIQUID PHASE ANALYSIS

[75] Inventors: Patrick Kaltenbach, Bischweier, Germany; Sally A. Swedberg, Los Altos, Calif.; Klaus E. Witt, Keltern; Fritz Bek, Waldbronn, both of Germany; Laurie S. Mittelstadt, Belmont, Calif.

[73] Assignee: Hewlett-Packard Company, Palo Alto, Calif.

[21] Appl. No.: 914,297

[22] Filed: Aug. 18, 1997

Related U.S. Application Data

[63] Continuation of Ser. No. 482,245, Jun. 7, 1995, Pat. No. 5,658,413, which is a continuation-in-part of Ser. No. 326,111, Oct. 19, 1994, Pat. No. 5,500,071.

[51] Int. Cl.[6] .................................................... B32B 31/00
[52] U.S. Cl. ........................ 156/257; 156/242; 156/272.8; 156/292; 264/156; 264/220; 264/328.1; 264/328.2
[58] Field of Search ............................... 156/64, 217, 242, 156/245, 257, 272.8, 290, 292; 95/82; 210/198.2, 656; 264/156, 220, 328.1, 328.2; 422/70

[56] References Cited

U.S. PATENT DOCUMENTS

| | | | |
|---|---|---|---|
| 5,500,071 | 3/1996 | Kaltenbach et al. | 156/272.8 |
| 5,571,410 | 11/1996 | Swedberg et al. | 210/198.2 |
| 5,641,400 | 6/1997 | Kaltenbach et al. | 210/198.2 |
| 5,645,702 | 7/1997 | Witt et al. | 204/501 |
| 5,658,413 | 8/1997 | Kaltenbach et al. | 156/272.8 |
| 5,669,997 | 9/1997 | Robbert et al. | 156/257 X |
| 5,688,355 | 11/1997 | Yu | 156/272.8 |

*Primary Examiner*—David A. Simmons
*Assistant Examiner*—Paul M. Rivard

[57] ABSTRACT

Miniaturized planar column devices are described for use in liquid phase analysis, the devices comprising microstructures fabricated by laser ablation in a variety of novel support substrates. Devices formed according to the invention include associated laser-ablated features required for function, such as analyte detection means and fluid communication means. Miniaturized columns constructed under the invention find use in any analysis system performed on either small and/or macromolecular solutes in the liquid phase and may employ chromatographic, electrophoretic, electrochromatographic separation means, or any combination thereof.

19 Claims, 15 Drawing Sheets

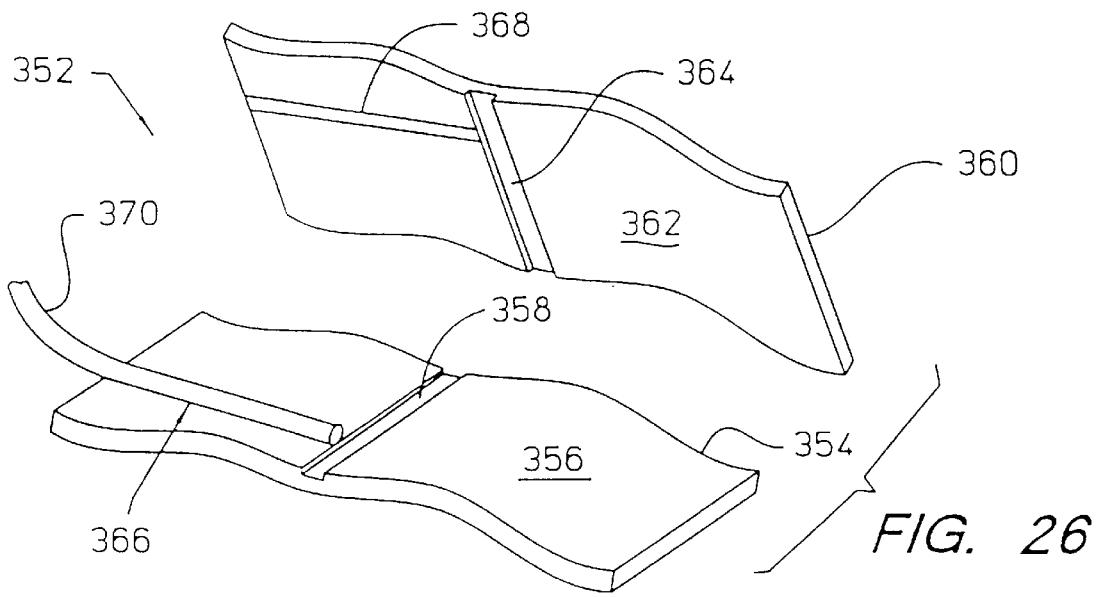
FIG. 26
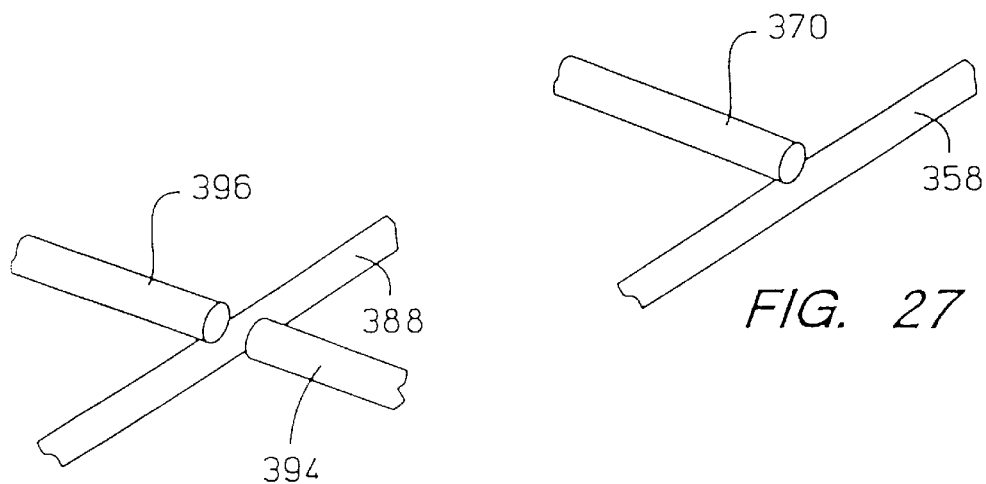
FIG. 27
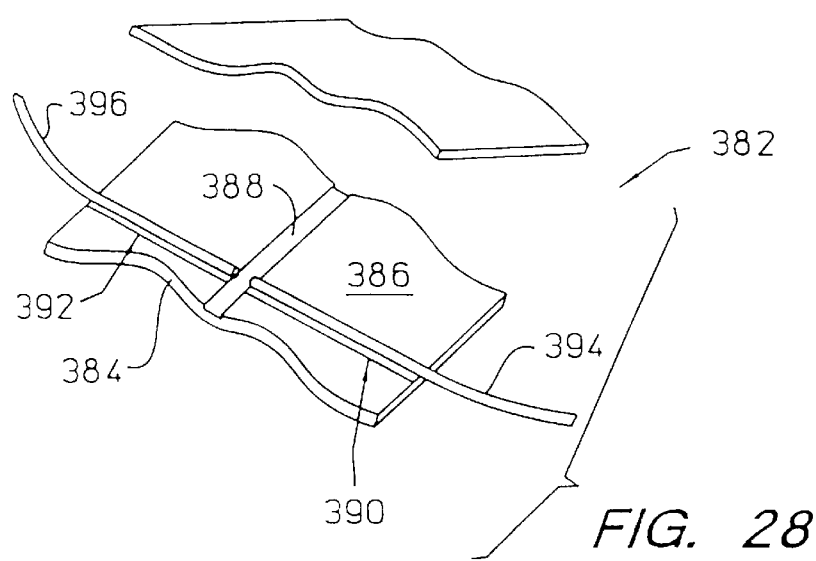
FIG. 29
FIG. 28

5,804,022

METHOD FOR MAKING MINIATURIZED PLANAR COLUMNS IN NOVEL SUPPORT MEDIA FOR LIQUID PHASE ANALYSIS

CROSS REFERENCE TO RELATED APPLICATIONS

This is a continuation of application Ser. No. 08/482,245 filed on Jun. 7, 1995, now U.S. Pat. No. 5,658,413, which is a continuation-in-part application of Ser. No. 08/326,111, filed on Oct. 19, 1994, now U.S. Pat. No. 5,500,071.

TECHNICAL FIELD

The present invention relates generally to miniaturized planar column technology for liquid phase analysis, and more particularly to fabrication of microstructures in novel separation support media using laser ablation techniques. The microstructures produced under the present invention find use in any analysis system which is performed on either small and/or macromolecular solutes in the liquid phase and which may employ chromatographic or electrophoretic means of separation, or a combination of both.

BACKGROUND OF THE INVENTION

In sample analysis instrumentation, and especially in separation systems such as liquid chromatography and capillary electrophoresis systems, smaller dimensions will generally result in improved performance characteristics and at the same time result in reduced production and analysis costs. In this regard, miniaturized separation systems provide more effective system design, result in lower overhead due to decreased instrumentation sizing and additionally enable increased speed of analysis, decreased sample and solvent consumption and the possibility of increased detection efficiency.

Accordingly, several approaches towards miniaturization for liquid phase analysis have developed in the art; the conventional approach using drawn fused-silica capillary, and an evolving approach using silicon micromachining. What is currently thought of as conventional in miniaturization technology is generally any step toward reduction in size of the analysis system.

In conventional miniaturized technology the instrumentation has not been reduced in size; rather, it is the separation compartment size which has been significantly reduced. As an example, micro-column liquid chromatography ($\mu$LC) has been described wherein columns with diameters of 100–200 $\mu$m are employed as compared to prior column diameters of around 4.6 mm.

Another approach towards miniaturization has been the use of capillary electrophoresis (CE) which entails a separation technique carried out in capillaries 25–100 $\mu$m in diameter. CE has been demonstrated to be useful as a method for the separation of a variety of large and small solutes. *J. Chromatog.* 218:209 (1981); *Analytical Chemistry* 53:1298 (1981). In contrast, polyacrylamide gel electrophoresis was originally carried out in tubes 1 mm in diameter. Both of the above described "conventional" miniaturization technologies ($\mu$LC and CE) represent a first significant step toward reducing the size of the chemical portion of a liquid phase analytical system. However, even though experimentation with such conventional miniaturized devices has helped to verify the advantages of miniaturization in principal, there nevertheless remain several major problems inherent in those technologies.

For example, there remains substantial detection limitations in conventional capillary electrophoresis technology. For example, in CE, optical detection is generally performed on-column by a single-pass detection technique wherein electromagnetic energy is passed through the sample, the light beam travelling normal to the capillary axis and crossing the capillary only a single time. Accordingly, in conventional CE systems, the detection path length is inherently limited by the diameter of the capillary.

Given Beer's law, which relates absorbance to the path length through the following relationship:

$A = \epsilon * b * C$ where:
 A=the absorbance
 $\epsilon$=the molar absorptivity, (l/m*cm)
 b=pathlength (cm)
 C=concentration (m/l)

it can be readily understood that the absorbance (A) of a sample in a 25 $\mu$m capillary would be a factor of 400× less than it would be in a conventional 1 cm pathlength cell as typically used in UV/Vis spectroscopy.

In light of this significant detection limitation, there have been a number of attempts employed in the prior art to extend detection path lengths, and hence the sensitivity of the analysis in CE systems. In U.S. Pat. No. 5,061,361 to Gordon, there has been described an approach entailing micro-manipulation of the capillary flow-cell to form a bubble at the point of detection. In U.S. Pat. No. 5,141,548 to Chervet, the use of a Z-shaped configuration in the capillary, with detection performed across the extended portion of the Z has been described. Yet another approach has sought to increase the detection pathlength by detecting along the major axis of the capillary (axial-beam detection). Xi et al., *Analytical Chemistry* 62:1580 (1990).

In U.S. Pat. No. 5,273,633 to Wang, a further approach to increased detection path lengths in CE has been described where a reflecting surface exterior of the capillary is provided, the subject system further including an incident window and an exit window downstream of the incident window. Under Wang, light entering the incident window passes through a section of the capillary by multiple internal reflections before passing through the exit window where it is detected, the subject multiple internal reflections yielding an effective increase in pathlength. While each of the aforementioned approaches has addressed the issue of extending the pathlength, each approach is limited in that it entails engineering the capillary after-the-fact or otherwise increasing the cost of the analysis.

A second major drawback in the current approach to miniaturization involves the chemical activity and chemical instability of silicon dioxide ($SiO_2$) substrates, such as silica, quartz or glass, which are commonly used in both CE and $\mu$LC systems. More particularly, silicon dioxide substrates are characterized as high energy surfaces and strongly adsorb many compounds, most notably bases. The use of silicon dioxide materials in separation systems is further restricted due to the chemical instability of those substrates, as the dissolution of $SiO_2$ materials increases in basic conditions (at pHs greater than 7.0).

To avoid the problems arising from the inherent chemical activity of silicon dioxide materials, prior separation systems have attempted chemical modifications to the inner silica surface of capillary walls. In general, such post-formation modifications are difficult as they require the provision of an interfacial layer to bond a desired surface treatment to the capillary surface, using, for example, silylating agents to create Si-O-Si-C bonds. Although such modifications may decrease the irreversible adsorption of solute molecules by the capillary surfaces, these systems still suffer from the chemical instability of Si-O-Si bonds at pH's above 7.0. Accordingly, chemical instability in $SiO_2$ materials remains a major problem.

However, despite the recognized shortcomings with the chemistry of $SiO_2$ substrates, those materials are still used in separation systems due to their desirable optical properties. In this regard, potential substitute materials which exhibit superior chemical properties compared to silicon dioxide materials are generally limited in that they are also highly adsorbing in the UV region, where detection is important.

In order to avoid some of the substantial limitations present in conventional $\mu$LC and CE techniques, and in order to enable even greater reduction in separation system sizes, there has been a trend towards providing planarized systems having capillary separation microstructures. In this regard, production of miniaturized separation systems involving fabrication of microstructures in silicon by micromachining or microlithographic techniques has been described. See, e.g. Fan et al., *Anal. Chem.* 66(1):177–184 (1994); Manz et al., *Adv. in Chrom.* 33:1–66 (1993); Harrison et al., *Sens. Actuators*, B B10(2):107–116 (1993); Manz et al., *Trends Anal. Chem.* 10(5):144–149 (1991); and Manz et al., *Sensors and Actuators B (Chemical)* B1(1–6):249–255 (1990).

The use of micromachining techniques to fabricate separation systems in silicon provides the practical benefit of enabling mass production of such systems. In this regard, a number of established techniques developed by the microelectronics industry involving micromachining of planar materials, such as silicon, exist and provide a useful and well accepted approach to miniaturization. Examples of the use of such micromachining techniques to produce miniaturized separation devices on silicon or borosilicate glass chips can be found in U.S. Pat. No. 5,194,133 to Clark et al.; U.S. Pat. No. 5,132,012 to Miura et al.; in U.S. Pat. No. 4,908,112 to Pace; and in U.S. Pat. No. 4,891,120 to Sethi et al.

Micromachining silicon substrates to form miniaturized separation systems generally involves a combination of film deposition, photolithography, etching and bonding techniques to fabricate a wide array of three dimensional structures. Silicon provides a useful substrate in this regard since it exhibits high strength and hardness characteristics and can be micromachined to provide structures having dimensions in the order of a few micrometers.

Although silicon micromachining has been useful in the fabrication of miniaturized systems on a single surface, there are significant disadvantages to the use of this approach in creating the analysis device portion of a miniaturized separation system.

Initially, silicon micromachining is not amenable to producing a high degree of alignment between two etched or machined pieces. This has a negative impact on the symmetry and shape of a separation channel formed by micromachining, which in turn may impact separation efficiency. Secondly, sealing of micromachined silicon surfaces is generally carried out using adhesives which may be prone to attack by separation conditions imposed by liquid phase analyses. Furthermore, under oxidizing conditions, a silica surface is formed on the silicon chip substrate. Thus, silicon micromachining is also fundamentally limited by the chemistry of $SiO_2$. Accordingly, there has remained a need for an improved miniaturized separation system which is able to avoid the inherent shortcomings of conventional miniaturization and silicon micromachining techniques.

SUMMARY OF THE INVENTION

The present invention relates to a miniaturized planar column device for use in a liquid phase analysis system. It is a primary object of the invention to provide a miniaturized column device laser-ablated in a substantially planar substrate, wherein the substrate is a material selected to avoid the inherent chemical activity and pH instability encountered with silicon and prior silicon dioxide-based device substrates.

The invention is also related to the provision of detection means engineered into a miniaturized planar column device whereby enhanced on-column analysis or detection of components in a liquid sample is enabled. It is a related object of the invention to provide a column device for liquid phase analysis having detection means designed into the device in significantly compact form as compared to conventional technology. It is a further object to provide optical detection means ablated in a miniaturized planar column device and having a substantially enhanced detection pathlength. It is yet a further object to provide a plurality of detection means which allow simultaneous interrogation of a liquid sample to detect separated analytes using multiple detection techniques that communicate with the sample at a particular position along the separation compartment.

In another aspect of the invention a device is provided which features improved means for liquid handling, including sample injection. In a related aspect, a miniaturized column device is provided having a means to interface with a variety of external liquid reservoirs. In a particular embodiment, a system design is provided which allows a variety of injection methods to be readily adapted to the planar structure, such as pressure injection, hydrodynamic injection or electrokinetic injection.

It is yet a further related object of the invention to provide a miniaturized total chemical analysis system ($\mu$-TAS) fully contained on a single, planar surface. Particularly, a miniaturized system according to the present invention is capable of performing complex sample handling, separation, and detection methods with reduced technician manipulation or interaction. Thus, the subject invention finds potential application in monitoring and/or analysis of components in industrial chemical, biological, biochemical and medical processes and the like.

A particular advantage provided by the invention is the use of processes other than silicon micromachining techniques or etching techniques to create miniaturized columns in a wide variety of polymeric and ceramic substrates having desirable attributes for an analysis portion of a separation system. More specifically, a miniaturized planar column device is formed herein by ablating component microstructures in a substrate using laser radiation. In one preferred embodiment, a miniaturized column device is formed by providing two substantially planar halves having microstructures laser-ablated thereon, which, when the two halves are folded upon each other, define a separation compartment featuring enhanced symmetry and axial alignment.

Use of laser ablation techniques to form miniaturized devices according to the invention affords several advantages over prior etching and micromachining techniques used to form systems in silicon or silicon dioxide materials. Initially, the capability of applying rigid computerized control over laser ablation processes allows microstructure formation to be executed with great precision, thereby enabling a heightened degree of alignment in structures formed by component parts. The laser ablation process also avoids problems encountered with microlithographic isotropic etching techniques which may undercut masking during etching, giving rise to asymmetrical structures having curved side walls and flat bottoms.

Laser ablation further enables the creation of microstructures with greatly reduced component size. In this regard, microstructures formed according to the invention are capable of having aspect ratios several orders of magnitude higher than possible using prior etching techniques, thereby providing enhanced separation capabilities in such devices. The use of laser-ablation processes to form microstructures in substrates such as polymers increases ease of fabrication and lowers per-unit manufacturing costs in the subject devices as compared to prior approaches such as micromachining devices in silicon. Devices formed under the invention in low-cost polymer substrates have the added feature of being capable of use as substantially disposable miniaturized column units.

In another aspect of the invention, laser-ablation in planar substrates allows for the formation of microstructures of almost any geometry or shape. This feature not only enables the formation of complex device configurations, but further allows for integration of sample preparation, sample injection, post-column reaction and detection means in a miniaturized total analysis system of greatly reduced overall dimensions.

The compactness of the analysis portion in a device formed herein—in conjunction with the feature that integral functions such as injection, sample handling and detection may be specifically engineered into the subject device to provide a $\mu$-TAS device—further allows for integrated design of system hardware to achieve a greatly reduced system footprint.

Thus, inherent weaknesses existing in prior approaches to liquid phase separation device miniaturization, and problems in using silicon micromachining techniques to form miniaturized column devices have been addressed. Accordingly, the present invention discloses a miniaturized column device capable of performing a variety of liquid phase analyses on a wide array of liquid samples.

BRIEF DESCRIPTION OF THE DRAWINGS

FIG. 26 is an exploded view of a miniaturized column device having an associated lightguide means disposed within a detection means.

FIG. 27 is a pictorial representation of the optional lightguide means communicating with the separation compartment of the device of FIG. 26.

FIG. 28 is an exploded view of a miniaturized column device having a plurality of associated lightguide means.

FIG. 29 is a pictorial representation of the plurality of lightguide means communicating with the separation compartment of the device of FIG. 28.

DETAILED DESCRIPTION OF THE PREFERRED EMBODIMENTS

Figure 1A:
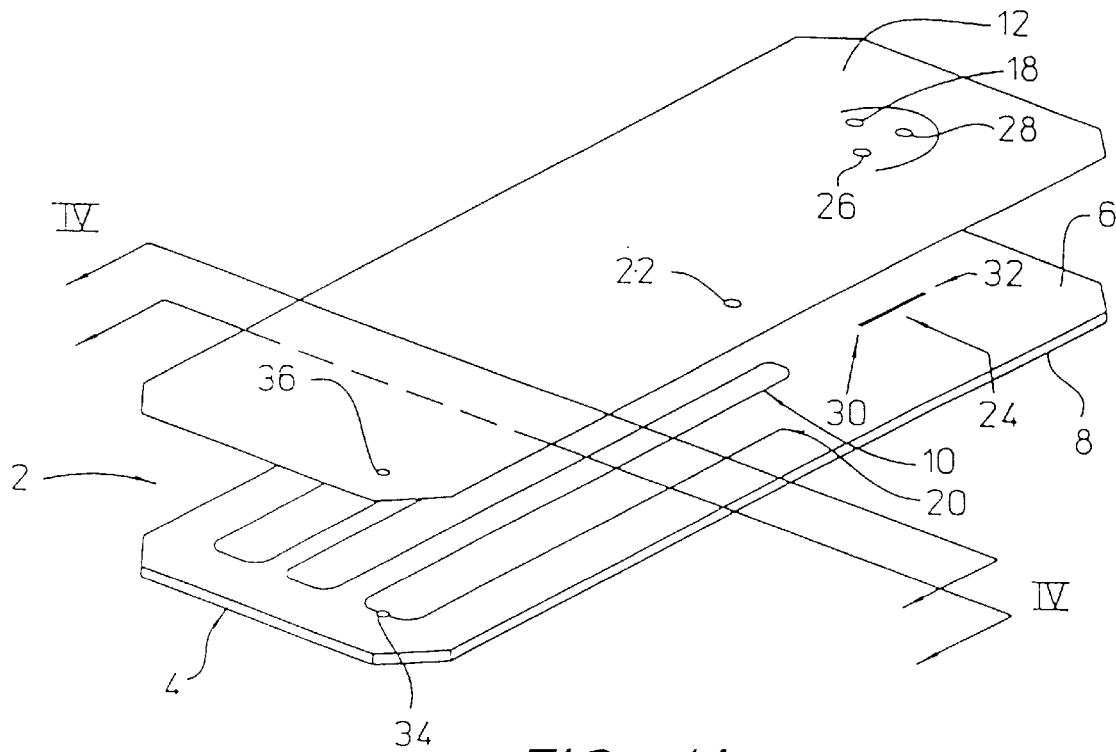
FIG. 1A is an exploded view of a miniaturized column device constructed in accordance with the invention.

Before the invention is described in detail, it is to be understood that this invention is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a," "an" and "the" include plural referents unless the context clearly dictates otherwise. Thus, for example, reference to "an analyte" includes mixtures of analytes, reference to "a detection means" includes two or more such detection means, and the like.

In this specification and in the claims which follow, reference will be made to a number of terms which shall be defined to have the following meanings:

The term "substrate" is used herein to refer to any material which is UV-adsorbing, capable of being laser-ablated and which is not silicon or a silicon dioxide material such as quartz, fused silica or glass (borosilicates). Accordingly, miniaturized column devices are formed herein using suitable substrates, such as laser ablatable polymers (including polyimides and the like) and ceramics (including aluminum oxides and the like). Further, miniaturized column devices are formed herein using composite substrates such as laminates. A "laminate" refers to a composite material formed from several different bonded layers of same or different materials. One particularly preferred composite substrate comprises a polyimide laminate formed from a first layer of polyimide such as Kapton®, available from DuPont (Wilmington, Del.), that has been co-extruded with a second, thin layer of a thermal adhesive form of polyimide known as KJ® available from DuPont (Wilmington, Del.). This thermoplastic adhesive layer can be on one or both sides of the first polyimide layer, thereby providing a laminate structure of any desired thickness.

As used herein, the term "detection means" refers to any means, structure or configuration which allows one to interrogate a sample within the separation compartment using analytical detection techniques well known in the art. Thus, a detection means includes one or more apertures, elongated apertures or grooves which communicate with the separation compartment and allow an external detection apparatus or device to be interfaced with the separation compartment to detect an analyte passing through the compartment.

Changes in the electrochemical properties of a liquid sample passing through the separation compartment can be detected using detection means which physically contact the sample passing through the separation compartment. In one embodiment, an electrode may be placed within, or butt-coupled to a detection means such as an aperture or a groove, thereby enabling the electrode to directly contact the sample stream. By arranging two dissimilar electrodes (which are connected through an external conducting circuit) opposite each other relative to the separation compartment, an electric field can be generated in the separation compartment—transverse to the direction of sample flow—thereby providing a ready means of electrochemical detection of analytes passing through the compartment.

Changes in the electrical properties of a liquid sample passing through the separation compartment can be detected using detection means which do not directly contact the sample passing through the separation compartment. Thus, "changes in the electrical properties" of a sample passing through the separation compartment refers to detectable changes in the conductivity, permittivity, or both of a particular sample due to the presence of an analyte in the sample. The "conductivity" of a sample refers to the ratio of the electric current density to the electric field in that sample. The "permittivity" of a sample refers to the dielectric constant of a sample multiplied by the permittivity of empty space, where the permittivity of empty space ($\epsilon_0$) is a constant appearing in Coulomb's law having the value of 1 in centimeter-gram-second electrostatic units.

Changes in the electrical properties of a sample passing through a separation compartment are measured herein by detection of the impedance of the liquid sample. The "impedance" or "electrical impedance" of a circuit refers to the total opposition that the circuit presents to an alternating current ("AC"), equal to the complex ratio of the voltage to the current in complex notation. Thus, the magnitude of the total opposition that a circuit presents to an alternating current is equal to the ratio of the maximum voltage in an AC circuit to the maximum current. An "electrical impedance meter" refers to an instrument which measures the complex ratio of voltage to current in a given circuit at a given frequency.

A plurality of electrical "communication paths" capable of carrying and/or transmitting electric current can be arranged adjacent to the separation compartment such that the communication paths, in combination, form a circuit. As used herein, a communication path includes any conductive material which is capable of transmitting or receiving an AC signal. A particularly preferred conductive material is copper. Thus, in one embodiment, a plurality of communication paths forming an antenna circuit (e.g., a pair of copper antennae) are arranged adjacent to the separation compartment whereby a circuit is formed capable of passing an oscillating voltage through the separation compartment which is sensitive to changes in the impedance of a liquid sample flowing therethrough. An "antenna" refers to a device capable of radiating and/or receiving radio waves such as an alternating current (AC) signal. An "antenna circuit" intends a complete electrical circuit which includes an antenna. An "antenna coil" refers to a coil through which antenna current (e.g., an AC signal) flows.

Further, by the arrangement of two detection means opposite each other relative to the separation compartment, a "detection path" is conveniently formed, thereby allowing detection of analytes passing through the separation compartment using detection techniques well known in the art.

An "optical detection path" refers to a configuration or arrangement of detection means to form a path whereby electromagnetic radiation is able to travel from an external source to a means for receiving radiation—wherein the radiation traverses the separation compartment and can be influenced by the sample or separated analytes in the sample flowing through the separation compartment. An optical detection path is generally formed under the invention by positioning a pair of detection means directly opposite each other relative to the separation compartment. In this configuration, analytes passing through the separation compartment can be detected via transmission of radiation orthogonal to the major axis of the separation compartment (and, accordingly, orthogonal to the direction of electro-osmotic flow in an electrophoretic separation). A variety of external optical detection techniques can be readily interfaced with the separation compartment using an optical detection path including, but not limited to, UV/Vis, Near IR, fluorescence, refractive index (RI) and Raman techniques.

As used herein, the term "transparent" refers to the ability of a substance to transmit light of different wavelengths, which ability may be measured in a particular substance as the percent of radiation which penetrates a distance of 1 meter. Thus, under the invention, a "transparent sheet" is defined as a sheet of a substance which is transmissive to specific types of radiation or particles of interest. Transparent sheets which are particularly employed in the invention in the context of optical detection configurations are formed from materials such as, but not limited to, quartz, sapphire, diamond and fused silica.

In the context of UV-visible absorption detection of sample analytes herein, the terms "path length," or "optical path length" refer to an optical path length "b" derived from Beer's law, which states that $$A = \log (I_i/I_f) = \epsilon * b * C$$

wherein A is the absorbance, $I_i$ is the light intensity measured in the absence of the analyte, $I_f$ is the light intensity transmitted through the analyte, $\epsilon$ is the molar extinction coefficient of the sample (l/m*cm), C is the analyte concentration (m/l), and b is the optical pathlength (cm). Thus, in a detection configuration wherein UV-vis absorption of a sample analyte is measured via an optical detection path by passing light through the separation compartment along a path perpendicular to the separation compartment major axis, the path length (b) of the measurement is substantially defined by the dimensions of the separation compartment.

A "detection intersection" refers to a configuration wherein a plurality of detection means that communicate with the separation compartment converge at a particular location in the separation compartment. In this manner, a number of detection techniques can be simultaneously performed on a sample or separated analyte at the detection intersection. Under the invention, a detection intersection is formed when a plurality of detection paths cross, or when a detection means such as an aperture communicates with the separation compartment at substantially the same point as a detection path. The sample, or a separated analyte, can thus be interrogated using a combination of UV/Vis and fluorescence techniques, optical and electrochemical techniques, optical and electrical techniques, or like combinations to provide highly sensitive detection information. See, e.g., Beckers et al. (1988) *J. Chromatogr.* 452:591–600; and U.S. Pat. No. 4,927,265, to Brownlee.

As used herein, a "lightguide means" refers to a substantially long, thin thread of a transparent substance which can be used to transmit light. Lightguide means useful in the practice of the invention include optical fibers, integrated lens configurations and the like. In particularly preferred embodiments, optical fibers are interfaced with detection means to enable optical detection techniques known in the art. The terms "optical fiber," "fiber optic waveguide" or "optical fiber means" are used herein to refer to a single optical fiber or a bundle optical fibers, optionally encased in a protective cladding material. Examples of suitable optical fiber substrate materials include glass, plastic, glass/glass composite and glass/plastic composite fibers. A critical characteristic of optical fibers is attenuation of an optical signal. Further, a chemical sensor can be incorporated into a fiber optic waveguide in a manner such that the chemical sensor will interact with the liquid sample analyte. Structures, properties, functions and operational details of such fiber optic chemical sensors can be found in U.S. Pat. No. 4,577,109 to Hirschfeld, U.S. Pat. No. 4,785,814 to Kane, and U.S. Pat. No. 4,842,783 to Blaylock.

The use of laser ablation techniques in the practice of the invention allows for a high degree of precision in the alignment of micro-scale components and structures, which alignment has either been difficult or not possible in prior silicon or glass substrate-based devices. Thus, the term "microalignment" as used herein refers to the precise and accurate alignment of laser-ablated features, including the enhanced alignment of complementary microchannels or microcompartments with each other, inlet and/or outlet ports with microchannels or separation compartments, detection means with microchannels or separation compartments, detection means with other detection means, and the like.

The term "microalignment means" is defined herein to refer to any means for ensuring the precise microalignment of laser-ablated features in a miniaturized column device. Microalignment means can be formed in the column devices either by laser ablation or other methods of fabricating shaped pieces, which methods are well known in the art. Representative microalignment means that can be employed herein include a plurality of coaxially arranged apertures laser-ablated in component parts and/or a plurality of corresponding features in column device substrates, e.g., projections and mating depressions, grooves and mating ridges or the like. Further, the accurate microalignment of component parts can be effected by forming the miniaturized columns in flexible substrates having at least one fold means laser-ablated therein, such that sections of the substrate can be folded to overlie other sections thereby forming composite micro-scale compartments, aligning features such as apertures or detection means with separation compartments, or forming micro-scale separation compartments from microchannels. Such fold means can be embodied by a row of spaced-apart perforations ablated in a particular substrate, spaced-apart slot-like depressions or apertures ablated so as to extend only part way through the substrate. The perforations or depressions can have circular, diamond, hexagonal or other shapes that promote hinge formation along a predetermined straight line.

The term "liquid phase analysis" is used to refer to any analysis which is done on either small and/or macromolecular solutes in the liquid phase. Accordingly, "liquid phase analysis" as used herein includes chromatographic separations, electrophoretic separations, and electrochromatographic separations.

In this regard, "chromatographic" processes generally comprise preferential separations of components, and include reverse-phase, hydrophobic interaction, ion exchange, molecular sieve chromatography and like methods.

"Electrophoretic" separations refers to the migration of particles or macromolecules having a net electric charge where said migration is influenced by an electric field. Accordingly electrophoretic separations include separations performed in columns packed with gels (such as polyacrylamide, agarose and combinations thereof) as well as separations performed in solution.

"Electrochromatographic" separations refers to combinations of electrophoretic and chromatographic techniques. Exemplary electrochromatographic separations include packed column separations using electromotive force (Knox et al. (1987) *Chromatographia* 24:135; Knox et al. (1989) *J. Liq. Chromatogr* 12:2435; Knox et al. (1991) *Chro-* matographia 32:317), and micellar electrophoretic separations (Terabe et al. (1985) *Anal. Chem.* 57:834–841).

The term "motive force" is used to refer to any means for inducing movement of a sample along a column in a liquid phase analysis, and includes application of an electric potential across any portion of the column, application of a pressure differential across any portion of the column or any combination thereof.

The term "surface treatment" is used to refer to preparation or modification of the surface of a microchannel which will be in contact with a sample during separation, whereby the separation characteristics of the device are altered or otherwise enhanced. Accordingly, "surface treatment" as used herein includes: physical surface adsorptions; covalent bonding of selected moieties to functional groups on the surface of microchannel substrates (such as to amine, hydroxyl or carboxylic acid groups on condensation polymers); methods of coating surfaces, including dynamic deactivation of channel surfaces (such as by adding surfactants to media), polymer grafting to the surface of channel substrates (such as polystyrene or divinyl-benzene) and thin-film deposition of materials such as diamond or sapphire to microchannel substrates.

The term "laser ablation" is used to refer to a machining process using a high-energy photon laser such as an excimer laser to ablate features in a suitable substrate. The excimer laser can be, for example, of the $F_2$, ArF, KrCl, KrF, or XeCl type.

In general, any substrate which is UV absorbing provides a suitable substrate in which one can laser ablate features. Accordingly, microstructures of selected configurations can be formed by imaging a lithographic mask onto a suitable substrate, such as a polymer or ceramic material, and then laser ablating the substrate with laser light in areas that are unprotected by the lithographic mask.

In laser ablation, short pulses of intense ultraviolet light are absorbed in a thin surface layer of material within about 1 $\mu$m or less of the surface. Preferred pulse energies are greater than about 100 millijoules per square centimeter and pulse durations are shorter than about 1 microsecond. Under these conditions, the intense ultraviolet light photodissociates the chemical bonds in the material. Furthermore, the absorbed ultraviolet energy is concentrated in such a small volume of material that it rapidly heats the dissociated fragments and ejects them away from the surface of the material. Because these processes occur so quickly, there is no time for heat to propagate to the surrounding material. As a result, the surrounding region is not melted or otherwise damaged, and the perimeter of ablated features can replicate the shape of the incident optical beam with precision on the scale of about one micrometer.

Although laser ablation has been described herein using an excimer laser, it is to be understood that other ultraviolet light sources with substantially the same optical wavelength and energy density may be used to accomplish the ablation process. Preferably, the wavelength of such an ultraviolet light source will lie in the 150 nm to 400 nm range to allow high absorption in the substrate to be ablated. Furthermore, the energy density should be greater than about 100 millijoules per square centimeter with a pulse length shorter than about 1 microsecond to achieve rapid ejection of ablated material with essentially no heating of the surrounding remaining material. Laser ablation techniques, such as those described above, have been described in the art. Znotins, T. A., et al., *Laser Focus Electro Optics*, (1987) pp. 54–70; U.S. Pat. Nos. 5,291,226 and 5,305,015 to Schantz et al.

The term "injection molding" is used to refer to a process for molding plastic or nonplastic ceramic shapes by injecting a measured quantity of a molten plastic or ceramic substrate into dies (or molds). In one embodiment of the present invention, miniaturized column devices can be produced using injection molding.

More particularly, a mold or die of a miniaturized column device is formed using excimer laser-ablation to define an original microstructure pattern in a suitable polymer substrate. The microstructure thus formed is then coated by a very thin metal layer and electroplated (such as by galvano forming) with a metal such as nickel to provide a carrier. When the metal carrier is separated from the original polymer, a mold insert (or tooling) is provided having the negative structure of the polymer. Multiple replicas of the ablated microstructure pattern can thus be manufactured in suitable polymer or ceramic substrates using injection molding techniques well known in the art.

The term "LIGA process" is used to refer to a process for fabricating microstructures having high aspect ratios and increased structural precision using synchrotron radiation lithography, galvanoforming, and plastic molding. In a LIGA process, radiation sensitive plastics are lithographically irradiated at high energy radiation using a synchrotron source to create desired microstructures (such as channels, ports, apertures and micro-alignment means), thereby forming a primary template.

The primary template is then filled with a metal by electrodeposition techniques. The metal structure thus formed comprises a mold insert for the fabrication of secondary plastic templates which take the place of the primary template. In this manner, highly accurate replicas of the original microstructures can be formed in a variety of substrates using injection or reactive injection molding techniques. The LIGA process has been described by Becker, E. W., et al., *Microelectric Engineering* 4 (1986) pp. 35–56. Descriptions of numerous polymer substrates which can be injection molded using LIGA templates, and which are suitable substrates in the practice of the subject invention, may be found in "Contemporary Polymer Chemistry", Allcock, H. R. and Lampe, F. W. (Prentice-Hall, Inc.) New Jersey (1981).

Accordingly, the invention concerns formation of miniaturized column devices using laser ablation in a suitable substrate. The column devices are also formed using injection molding techniques wherein the original microstructure has been formed by an excimer laser ablation process, or where the original microstructure has been formed using a LIGA process.

More particularly, microstructures such as separation compartments, injection means, detection means and micro-alignment means can be formed in a planar substrate by excimer laser ablation. A frequency multiplied YAG laser can also be used in place of the excimer laser. In such a case, a complex microstructure pattern useful for practicing the invention can be formed on a suitable polymeric or ceramic substrate by combining a masking process with a laser ablation means, such as in a step-and-repeat process, where such processes would be readily understood by one of ordinary skill in the art.

In the practice of the invention, a preferred substrate comprises a polyimide material such as those available under the trademarks Kapton® or Upilex® from DuPont (Wilmington, Del.), although the particular substrate selected can comprise any other suitable polymer or ceramic substrate. Polymer materials particularly contemplated herein include materials selected from the following classes: polyimide, polycarbonate, polyester, polyamide, polyether, polyolefin, or mixtures thereof. Further, the polymer material selected can be produced in long strips on a reel, and, optional sprocket holes along the sides of the material may be provided to accurately and securely transport the substrate through a step-and-repeat process.

The selected polymer material is transported to a laser processing chamber and laser-ablated in a pattern defined by one or more masks using laser radiation. In a preferred embodiment, such masks define all of the ablated features for an extended area of the material, for example encompassing multiple apertures (including inlet and outlet ports), micro-alignment means and separation chambers.

Alternatively, patterns such as the aperture pattern, the separation channel pattern, etc., can be placed side by side on a common mask substrate which is substantially larger than the laser beam. Such patterns are then moved sequentially into the beam. In other production methods, one or more masks can be used to form apertures through the substrate, and another mask and laser energy level (and/or number of laser shots) can be used to define separation channels which are only formed through a portion of the thickness of the substrate. The masking material used in such masks is, preferably, highly reflecting at the laser wavelength, consisting of, for example, a multilayer dielectric material or a metal such as aluminum.

The laser ablation system employed in the invention generally includes beam delivery optics, alignment optics, a high precision and high speed mask shuttle system, and a processing chamber including mechanism for handling and positioning the material. In a preferred embodiment, the laser system uses a projection mask configuration wherein a precision lens interposed between the mask and the substrate projects the excimer laser light onto the substrate in the image of the pattern defined on the mask.

It will be readily apparent to one of ordinary skill in the art that laser ablation can be used to form miniaturized separation channels and apertures in a wide variety of geometries. Any geometry which does not include undercutting can be provided using ablation techniques, such as modulation of laser light intensity across the substrate, stepping the beam across the surface or stepping the fluence and number of pulses applied to each location to control corresponding depth. Further, laser-ablated channels or chambers produced according to the invention are easily fabricated having ratios of channel depth to channel width which are much greater than previously possible using etching techniques such as silicon micromachining. Such aspect ratios can easily exceed unity, and may even reach to 10.

In a preferred embodiment of the invention, channels of a semi-circular cross-section are laser ablated by controlling exposure intensity or by making multiple exposures with the beam being reoriented between each exposure. Accordingly, when a corresponding semi-circular channel is aligned with a channel thus formed, a separation chamber of highly symmetrical circular cross-section is defined which may be desirable for enhanced fluid flow through the separation device.

As a final step in laser ablation processes contemplated by the invention, a cleaning step is performed wherein the laser-ablated portion of the substrate is positioned under a cleaning station. At the cleaning station, debris from the laser ablation are removed according to standard industry practice.

"Optional" or "optionally" as used herein means that the subsequently described feature or structure may or may not be present on the miniaturized column device, or that the subsequently described event or circumstance may or may not occur; and that the description includes instances where a particular feature or structure is present and instances where the feature or structure is absent, or instances where the event or circumstance occurs and instances where it does not. For example, the phrase "a column device optionally having microalignment means" intends that microalignment means may or may not be present on the device and that the description includes both circumstances where such means are present and absent.

As will be appreciated by those working in the field of liquid phase analysis devices, the above-described method can be used to produce a wide variety of miniaturized devices. One such device is represented in FIG. 1A where a particular embodiment of a miniaturized column device is generally indicated at 2. The miniaturized column 2 is formed in a selected substrate 4 using laser ablation techniques. The substrate 4 generally comprises first and second substantially planar opposing surfaces indicated at 6 and 8 respectively, and is selected from a material other than silicon which is UV absorbing and, accordingly, laser-ablatable.

In a particular embodiment of the invention, the miniaturized column device 2 comprises a column structure ablated on a chip, which, in the practice of the invention may be a machinable form of the plastic polyimide such as Vespel®. The use of this particular polyimide substrate is preferred as, based on considerable experience with the shortcomings of fused silica and research into alternatives thereof, polyimides have proved to be a highly desirable substrate material for the analysis portion of a liquid phase separation system.

In this regard, it has been demonstrated that polyimides exhibit low sorptive properties towards proteins, which are known to be particularly difficult to analyze in prior silicon dioxide-based separation systems. Successful demonstrations of separations with this difficult class of solutes typically ensures that separation of other classes of solutes will be not be problematic. Further, since polyimide is a condensation polymer, it is possible to chemically bond groups to the surface which can provide a variety of desirable surface properties, depending on the target analysis. Unlike prior silicon dioxide based systems, these bonds to the polymeric substrate demonstrate pH stability in the basic region (pH 9–10).

Figure 2:
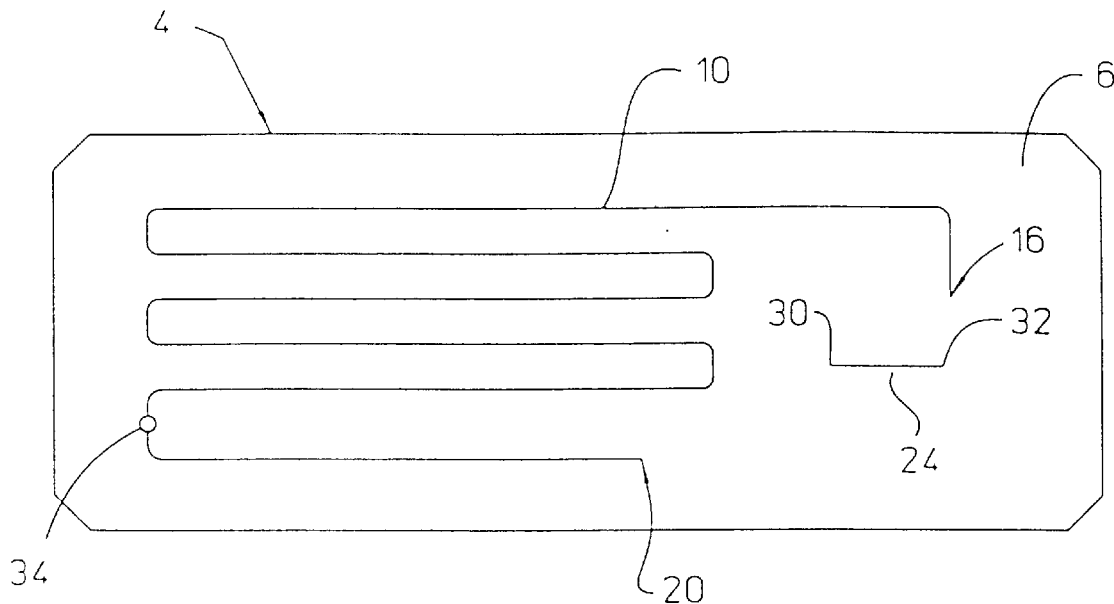
FIG. 2 is a plan view of the interior surface of the miniaturized column device of FIG. 1A.
Figure 3:
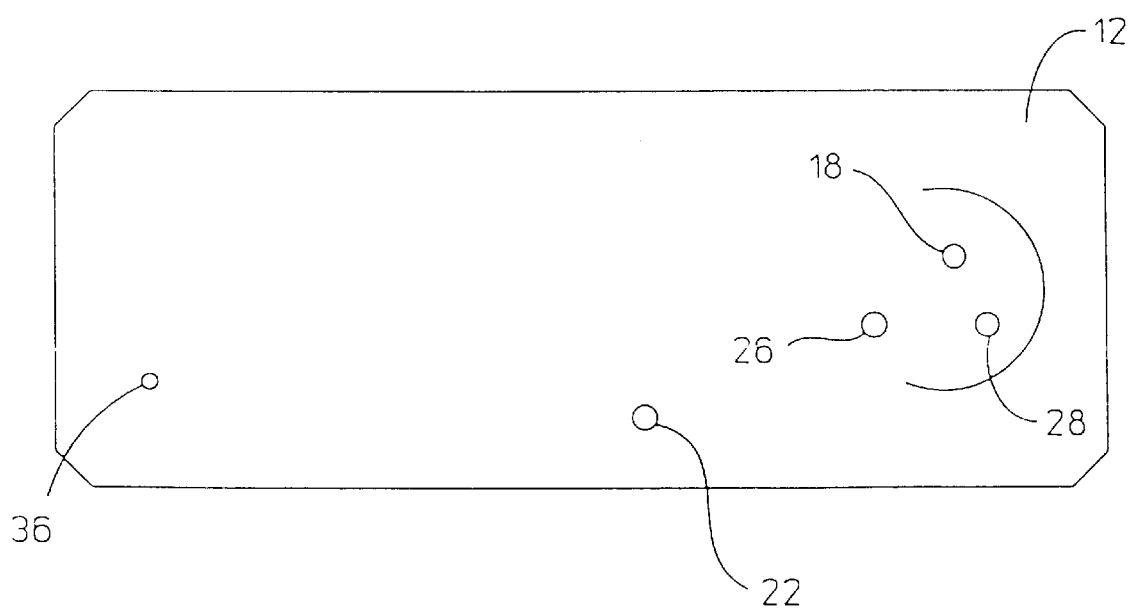
FIG. 3 is a plan view of the exterior surface of the device of FIG. 1A.

Referring now to FIGS. 1A, 2 and 3, the substrate 4 has a microchannel 10 laser-ablated in a first planar surface 6. It will be readily appreciated that, although the microchannel 10 has been represented in a generally extended form, microchannels formed under the invention can be ablated in a large variety of configurations, such as in a straight, serpentine, spiral, or any tortuous path desired. Further, as described above, the microchannel 10 can be formed in a wide variety of channel geometries including semi-circular, rectangular, rhomboid, and the like, and the channels can be formed in a wide range of aspect ratios. It is also noted that a device having a plurality of microchannels laser-ablated thereon falls within the spirit of the invention.

Figure 4:
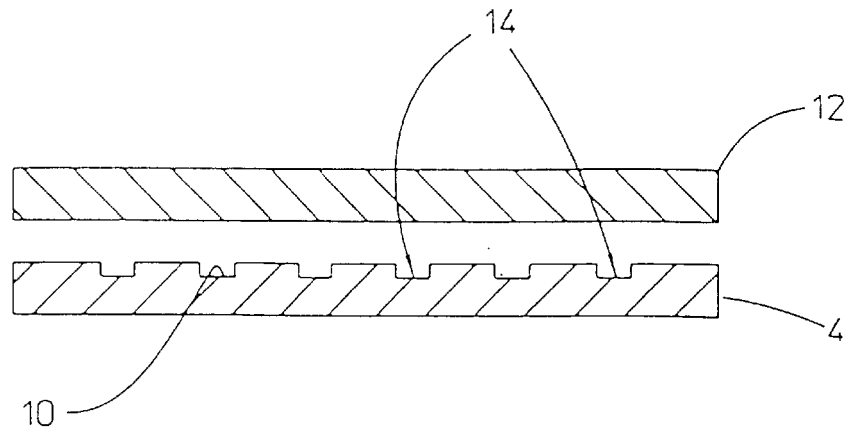
FIG. 4 is a cross-sectional side view of the miniaturized column device of FIG 1A, taken along lines IV—IV and showing formation of a separation compartment according to the invention.

Referring particularly to FIGS. 1A and 4, a cover plate 12 is arranged over the first planar surface 6 and, in combination with the laser-ablated microchannel 10, forms an elongate separation compartment 14. The cover plate 12 can be formed from any suitable substrate such as polyimide, where the selection of the substrate is limited only by avoidance of undesirable separation surfaces such as silicon or silicon dioxide materials.

In various embodiments, the cover plate 12 can be fixably aligned over the first planar surface 6 to form a liquid-tight separation compartment by using pressure sealing techniques, by using external means to urge the pieces together (such as clips, tension springs or associated clamping apparatus) or by using adhesives well known in the art of bonding polymers, ceramics and the like.

Referring to FIGS. 1A and 2–4, a particular embodiment of the invention is shown wherein the cover plate 12 further includes apertures which have been ablated therein. Particularly, a first aperture communicates with the separation compartment 14—which has been formed by the combination of microchannel 10 and cover plate 12—at a first end 16 thereof to form an inlet port 18 enabling the passage of fluid from an external source into the separation compartment. A second aperture communicates with the separation compartment 14 at a second end 20 thereof to form an outlet port 22 enabling passage of fluid from the separation compartment to an external receptacle. Accordingly, a miniaturized column device is formed having a flow path extending from the first end 16 of the separation compartment and passing to the second end 20 thereof, whereby liquid phase analysis of samples can be carried out using techniques well known in the art.

Referring still to FIGS 1A and 2–4, a particular embodiment of the invention is shown including sample introduction means laser-ablated into both the substrate 4 and cover plate 12. An internally ablated by-pass channel 24 is formed in substrate 4, such that the channel 24 is disposed near the first end 16 of the separation compartment. Two additional apertures 26 and 28 are formed in cover plate 12 and are arranged to cooperate with first and second ends (indicated at 30 and 32 respectively) of the by-pass channel 24. In this manner, a sample being held in an external reservoir can be introduced into by-pass channel 24 to form a sample plug of a known volume (defined by the dimensions of the channel 24). The sample plug thus formed can then be introduced into the first end 16 of the separation compartment 14 via inlet port 18 by communicating external mechanical valving with the inlet port and laser-ablated apertures 26 and 28 and flushing solution through the by-pass channel 24 into the separation compartment.

It is noted that the ablated by-pass channel 24 and apertures 26 and 28 further enable a wide variety of sample introduction techniques to be practiced. Particularly, having a by-pass channel which is not connected to the separation compartment allows a user to flush a sample through the by-pass channel without experiencing sample carry-over or column contamination. As will be appreciated by one of ordinary skill in the art after reading this specification, one such sample introduction technique can be effected by butt-coupling an associated rotor to a stator (not shown) on the external surface of a miniaturized column where the rotor selectively interfaces external tubing and fluid sources with the inlet port 18 and apertures 26 and 28. In this manner, the rotor allows a sample to be flushed from the by-pass channel 24 into external tubing—from which tubing the sample can then be introduced into the column via the inlet port 18 for liquid phase analysis thereof. Thus, a miniaturized column device formed in a polyimide substrate enables a ceramic rotor—pressed to the device using tensioned force (to form a liquid-tight seal)—to still rotate between selected aperture positions on the device due to the friction characteristics of the two materials. Other suitable rotors can be formed in rigid materials such as, but not limited to, glass and non-conductive substrates.

Accordingly, in the practice of the invention, external hardware provides the mechanical valving necessary for communication of a miniaturized column device to different external liquid reservoirs, such as an electrolyte solution, flush solution or the sample via laser-ablated holes designed into the cover plate 12. This feature allows a variety of injection methods to be adapted to a miniaturized planar column device, including pressure injection, hydrodynamic injection or electrokinetic injection. In the particular embodiment of FIGS. 1A, 2 and 3, the external valving and injection means can communicate with the separation device by butt-coupling to the laser-ablated apertures; however, any other suitable method of connection known in the art can be readily adapted to the invention. Further, it is noted that numerous other sample introduction and fluid interfacing designs can be practiced and still fall within the spirit of the subject invention.

Referring still to FIGS. 1A and 2–4, a wide variety of means for applying a motive force along the length of the separation compartment 14 can be associated with the subject device. Particularly, a pressure differential or electric potential can be applied along the entire length of the separation compartment by interfacing motive means with the inlet port 18 and outlet port 22 using techniques well known in the art.

The use of substrates such as polyimides in the construction of miniaturized columns herein allows the possibility of using refractive-index (RI) detection to detect separated analytes of interest passing through the subject columns. In this manner, the provision of an associated laser diode which emits radiation at a wavelength where polyimide is "transparent" (such as at >500 nm) allows for a detection setup where no additional features need to be ablated in the column devices.

Referring particularly to FIGS. 2–4, in another preferred embodiment of the invention, one or more detection means can optionally be ablated into the substrate 4 and/or cover plate 12. Preferably, the detection means will be disposed substantially downstream of the first end 16 of the separation compartment 14 to enable detection of separated analytes from the liquid sample. More specifically, an aperture 34 can be ablated through substrate 4 to communicate with the separation compartment 14. A corresponding aperture 36 can likewise be formed in cover plate 12, and arranged so that it will be in coaxial alignment with aperture 34 when the cover plate is affixed to the substrate to form the separation compartment 14. In this manner, electrodes (not shown) can be connected to the miniaturized column device via the apertures 34 and 36 to detect separated analytes of interest passing through the separation compartment by electrochemical detection techniques.

Figure 5:
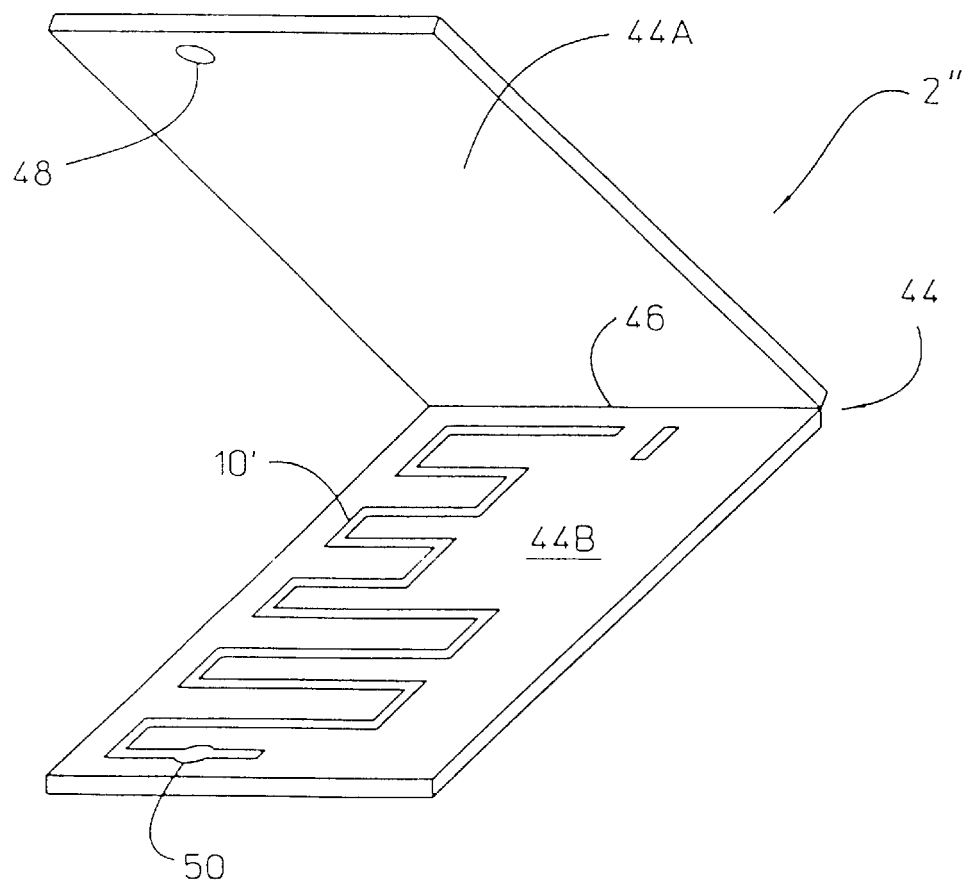
FIG. 5 is a plan view of a preferred embodiment of the miniaturized column device of FIG. 1A which is constructed from a single flexible substrate.

Referring now to FIG. 5, a related aspect of the invention is shown, comprising a miniaturized column device 2", wherein the column portion and the cover plate portion are formed in a single, flexible substrate indicated at 44. The flexible substrate 44 thus includes first and second portions, 44A and 44B, respectively, wherein each portion has a substantially planar interior surface. First and second portions 44A and 44B are separated by at least one fold means 46, such that the first portion can be readily folded to overlie the second portion. In particularly preferred embodiments, fold means 46 can comprise a row of spaced-apart perforations ablated in the flexible substrate, spaced-apart slot-like depressions or apertures ablated so as to extend only part way through the substrate, or the like. The perforations or depressions can have circular, diamond, hexagonal or other shapes that promote hinge formation along a predetermined straight line.

Thus, the miniaturized column device 2" is formed by first laser ablating a microchannel 10' in the second substrate portion 44B. A separation compartment is then provided by folding the flexible substrate 44 at the fold means 46 such that the first portion 44A covers the microchannel 10' to form a separation compartment as described above.

In this manner, the accurate alignment of various component parts is readily enabled by the provision of fold means 46. More particularly, such fold means 46 allows the first and second portions 44A and 44B to hingably fold upon each other to accurately align components which have been ablated in the first and second portions. In one particular embodiment, a detection means 48 is provided which is formed by ablating an aperture in the first portion 44A of the flexible substrate. The detection means 48 is arranged to communicate with the microchannel 10' when the portions 44A and 44B are folded upon each other. In a related embodiment, the detection means 48 is arranged to correspond with another detection means 50, comprising an aperture which has been laser ablated in the second portion 44B to communicate with the microchannel 10'. Thus, when the portions 44A and 44B are folded upon each other, a coaxial detection path is provided by the alignment of the corresponding detection means 48 and 50. In this manner, the coaxially aligned detection means enable optical detection of separated analytes passing through separation compartment via transmission of radiation orthogonal to the major axis of the separation compartment (and, accordingly, orthogonal to the direction of electro-osmotic flow in an electrophoretic separation).

In yet further related aspects of the invention, optional micro-alignment means—formed either by laser ablation techniques or by other methods of fabricating shaped pieces well known in the art—are provided in the miniaturized column devices 2 and/or 2" of FIGS. 1A and 5, respectively. More specifically, a plurality of corresponding laser-ablated apertures (not shown) can be provided in either the substrate 4 and cover plate 12, or in the first and second flexible substrate portions 44A and 44B. The subject apertures are arranged such that coaxial alignment thereof enables the precise alignment of the substrate 4 with the cover plate 12, or of the first and second flexible substrate portions 44A and 44B to align various features such as detection means with an ablated elongate bore. Such optional alignment can be effected using an external apparatus with means (such as pins) for cooperating with the coaxial apertures to maintain the components or portions in proper alignment with each other.

Figure 1B:
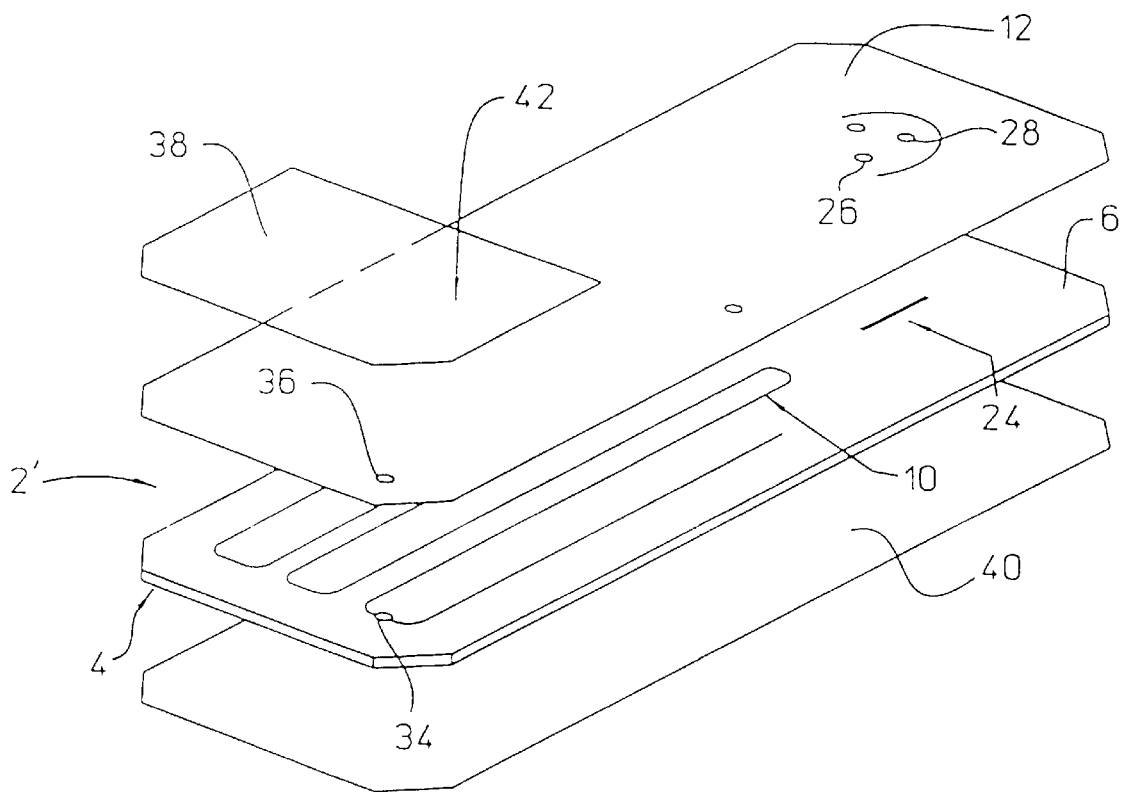
FIG. 1B is an exploded view of a preferred embodiment of the present invention including optical detection means.

Referring now to FIG. 1B, a further embodiment of the invention, indicated at 2' is shown comprising a preferred detection means indicated generally at 42. More particularly, a first transparent sheet 38 is provided wherein the cover plate 12 is interposed between the first transparent sheet and substrate 4. A second transparent sheet 40 is also provided wherein the second sheet is disposed over the second planar surface 8 of the substrate 4. In this manner, detection means 42 allows optical detection of separated analytes passing through a separation compartment—that has been formed by the combination of microchannel 10 and cover plate 12—via transmission of radiation orthogonal to the major axis of the separation compartment (and, accordingly, orthogonal to the direction of electro-osmotic flow in an electrophoretic separation). Further, in the practice of the invention, the transparent sheets can comprise materials such as quartz, diamond, sapphire, fused silica or any other suitable substrate which enables light transmission therethrough.

The subject transparent sheets can be formed with just enough surface area to cover and seal the detection apertures 34 and 36, or those sheets can be sized to cover up to the entire surface area of the column device. In this regard, additional structural rigidity is provided to a column device formed in a particularly thin substrate film, such as a thin-film polyimide substrate, by employing a substantially co-extensive planar sheet of, for example, fused silica.

Accordingly, the above described optical detection means 42 enables adaptation of a variety of external optical detection means to miniaturized columns constructed according to the invention. Further, sealing of the transparent sheets 38 and 40 to the miniaturized column device 2' is readily enabled, for example, when substrate 4 and cover plate 12 are formed in polyimide materials which include a layer of a thermal adhesive form of polyimide, since it is known that quartz/Kapton® bonds formed using such adhesives are very resilient. Sealing of other preferred transparent sheet materials, such as diamond, sapphire or fused-silica to the subject device can be accomplished using adhesion techniques well known in the art.

The capability of detecting with radiation over a range of electromagnetic wavelengths offers a variety of spectrophotometric detection techniques to be interfaced with a miniaturized column according to the invention, including, but not limited to, near IR, UV/Vis, fluorescence, refractive index (RI) and Raman.

Further, as will be readily appreciated, the use of optical detection means comprising apertures ablated into the substrate and cover plate provides great control over the effective detection pathlength in a miniaturized column device constructed herein. In this regard, the detection pathlength will be substantially equal to the combined thickness of the substrate 4 and the cover plate 12, and detection path lengths of up to 250 $\mu$m are readily obtainable using the subject detection means 42 in thin-film substrates such as polyimides.

Figure 6:
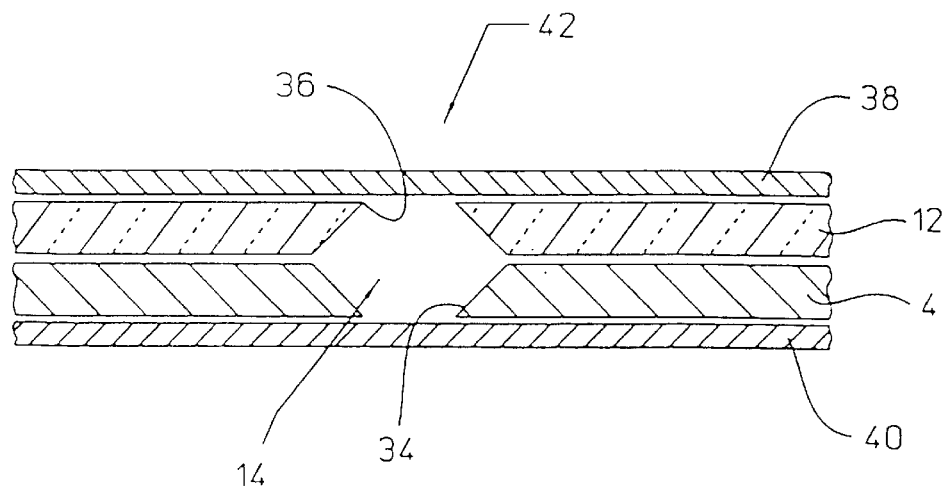
FIG. 6 is a cross-sectional axial view of the intersection of the separation compartment and the optical detection means in the miniaturized column device of FIG. 1B.

Referring now to FIG. 6, it can be seen that apertures 34 and 36 provide an enlarged volume in separation compartment 14 at the point of intersection with the detection means 42, where the enlarged volume will be proportional to the combined thickness of substrate 4 and cover plate 12. In this manner, sample plugs passing through separation compartment 14 can be subject to untoward distortion as the plug is influenced by the increased compartment volume in the detection area, especially where the combined thickness of the substrate and cover plate exceeds about 250 $\mu$m, thereby possibly reducing separation efficiency in the device.

Accordingly, in the present invention wherein detection path lengths exceeding 250 $\mu$m are desired, an alternative device embodiment is provided having laser-ablated features on two opposing surfaces of a substrate. More particularly, in FIGS. 7A and 7B, a further embodiment of a miniaturized column device is generally indicated at 52. The miniaturized column comprises a substrate 54 having first and second substantially planar opposing surfaces respectively indicated at 56 and 58. The substrate 54 has a first microchannel 60 laser ablated in the first planar surface 56 and a second microchannel 62 laser ablated in the second planar surface 58, wherein the microchannels can be provided in a wide variety of geometries, configurations and aspect ratios as described above.

Figure 7A:
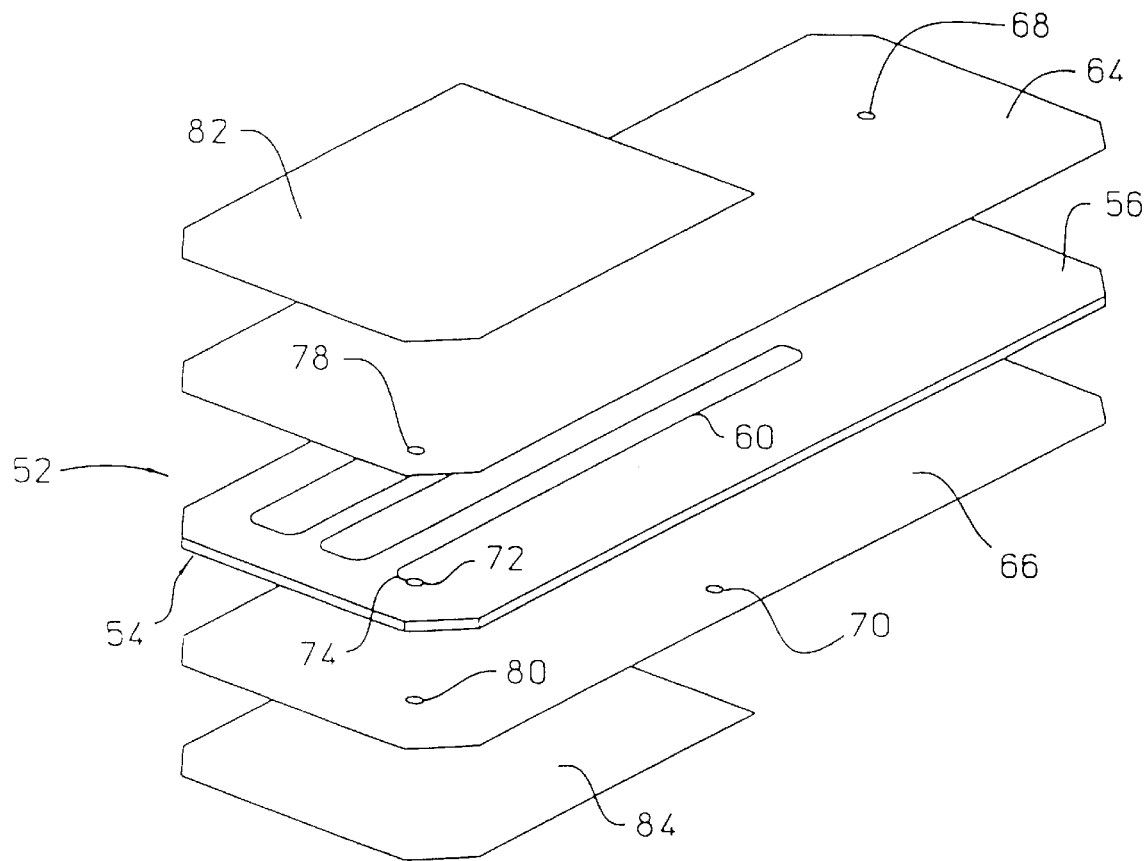
FIG. 7A is an exploded view of a first side of a miniaturized column device having microchannels formed on two opposing planar surfaces of a support substrate.
Figure 7B:
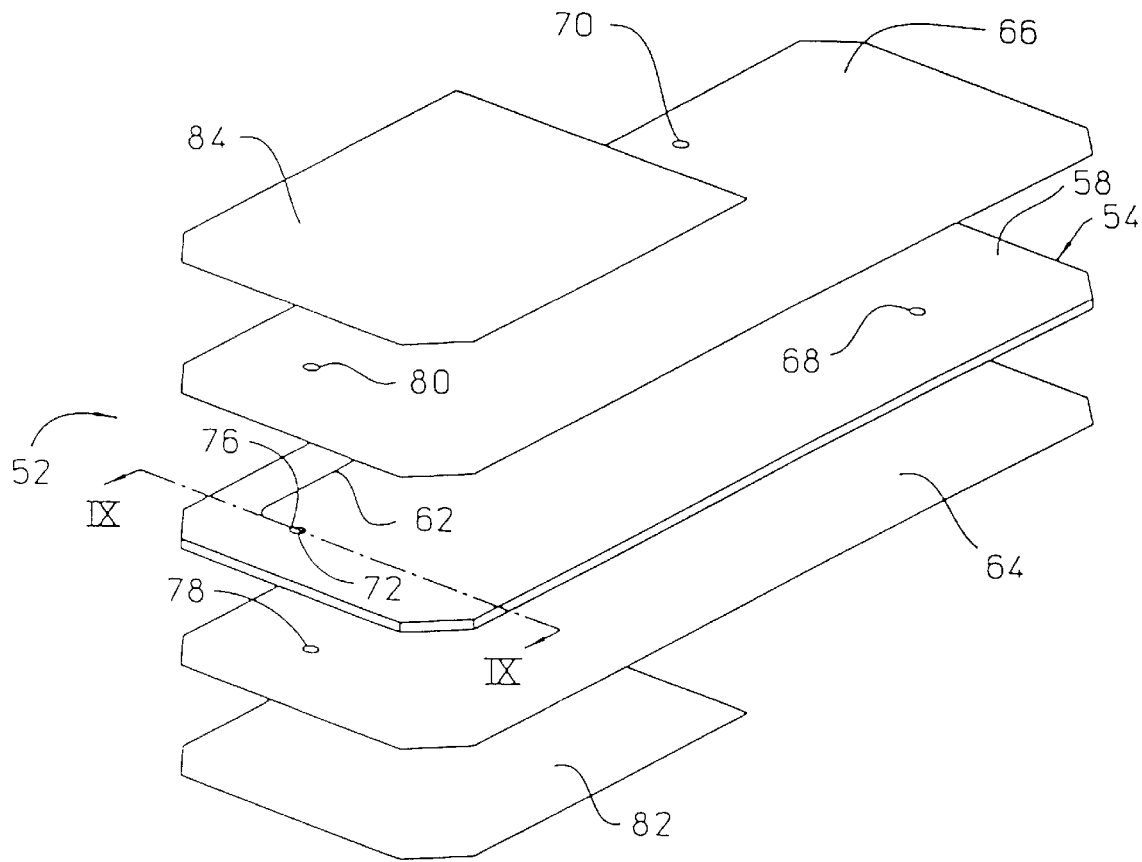
FIG. 7B is an exploded view of a second side of the column device of FIG. 7A.

The miniaturized column device of FIGS. 7A and 7B further includes first and second cover plates, indicated at 64 and 66 respectively, which, in combination with the first and second microchannels 60 and 62, define first and second elongate separation compartments when substrate 54 is sandwiched between the first and second cover plates.

Referring still to FIGS. 7A and 7B, a plurality of apertures can be laser-ablated in the device to provide an extended separation compartment, and further to establish fluid communication means. More particularly, a conduit means 72, comprising a laser ablated aperture in substrate 54 having an axis which is orthogonal to the first and second planar surfaces 56 and 58, communicates a distal end 74 of the first microchannel 60 with a first end 76 of the second microchannel 62 to form an extended separation compartment.

Further, an aperture 68, laser ablated in the first cover plate 64, enables fluid communication with the first microchannel 60, and a second aperture 70, laser ablated in the second cover plate 66, enables fluid communication with the second microchannel 62. As will be readily appreciated, when the aperture 68 is used as an inlet port, and the second aperture 70 is used as an outlet port, a miniaturized column device is provided having a flow path extending along the combined length of the first and second microchannels 60 and 62.

In the embodiment of the invention as shown in FIGS. 7A and 7B, a wide variety of sample introduction means can be employed, such as those described above. External hardware can also be interfaced to the subject device to provide liquid handling capabilities, and a variety of means for applying a motive force along the length of the separation compartment can be associated with the device, such as by interfacing motive means with the first and/or second apertures 68 and 70 as described above.

Additionally, a variety of detection means are easily included in the subject embodiment. In this regard, a first aperture 78 can be laser ablated in the first cover plate 64, and a second aperture 80 can likewise be formed in the second cover plate 66 such that the first and second apertures will be in coaxial alignment with conduit means 72 when the substrate 54 is sandwiched between the first and second cover plates. Detection of analytes in a separated sample passing through the conduit means is thereby easily enabled, such as by connecting electrodes to the miniaturized column via apertures 78 and 80 and detecting using electrochemical techniques.

Figure 9:
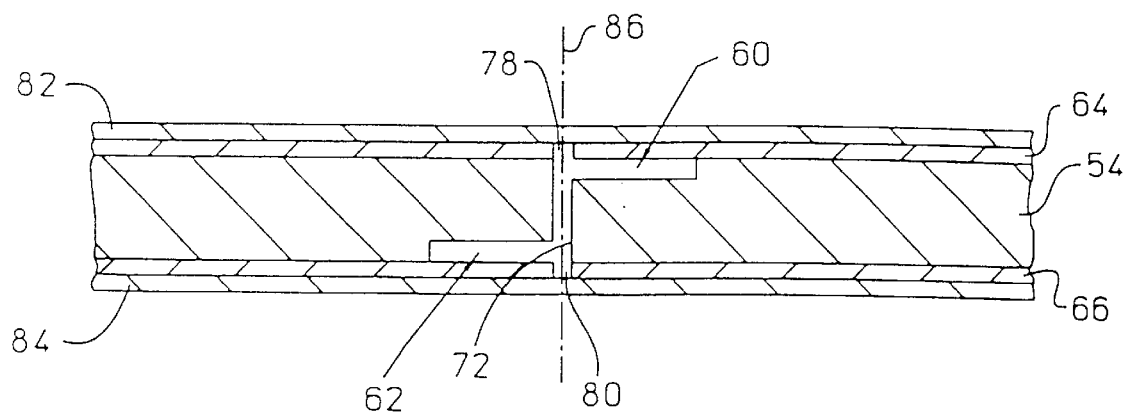
FIG. 9 is a cross-sectional trans-axial view of the extended optical detection pathlength in the miniaturized column of FIG. 7B taken along lines IX—IX.

However, a key feature of the laser-ablated conduit means 72 is the ability to provide an extended optical detection path length of up to 1 mm, or greater, without experiencing untoward sample plug distortion due to increased separation compartment volumes at the point of detection. Referring to FIGS. 7A, 7B and 9, first and second transparent sheets, indicated at 82 and 84 respectively, can be provided such that the first cover plate 64 is interposed between the first transparent sheet and the first planar surface 56, and the second cover plate 66 is interposed between the second transparent sheet and the second planar surface 58. The transparent sheets 82 and 84 can be selected from appropriate materials such as quartz crystal, fused silica, diamond, sapphire and the like. Further, the transparent sheets can be provided having just enough surface area to cover and seal the apertures 78 and 80, or those sheets can be sized to cover up to the entire surface area of the column device. As described above, this feature allows additional structural rigidity to be provided to a column device formed in a particularly thin substrate.

As best shown in FIG. 9, the subject arrangement allows optical detection of sample analytes passing through the miniaturized column device to be carried out along an optical detection path length 86 corresponding to the major axis of the conduit means 72. As will be readily appreciated, the optical detection path length 86 is substantially determined by the thickness of the substrate 54, and, accordingly, a great deal of flexibility in tailoring a miniaturized column device having μ-meter column dimensions and optical path lengths of up to 1 mm or greater is thereby enabled herein. In this manner, a wide variety of associated optical detection devices can be interfaced with the novel miniaturized columns, and detection of analytes in samples passing through the conduit means 72 can be readily carried out using UV/Vis, fluorescence, refractive index (RI), Raman and like spectrophotometric techniques.

Figure 8A:
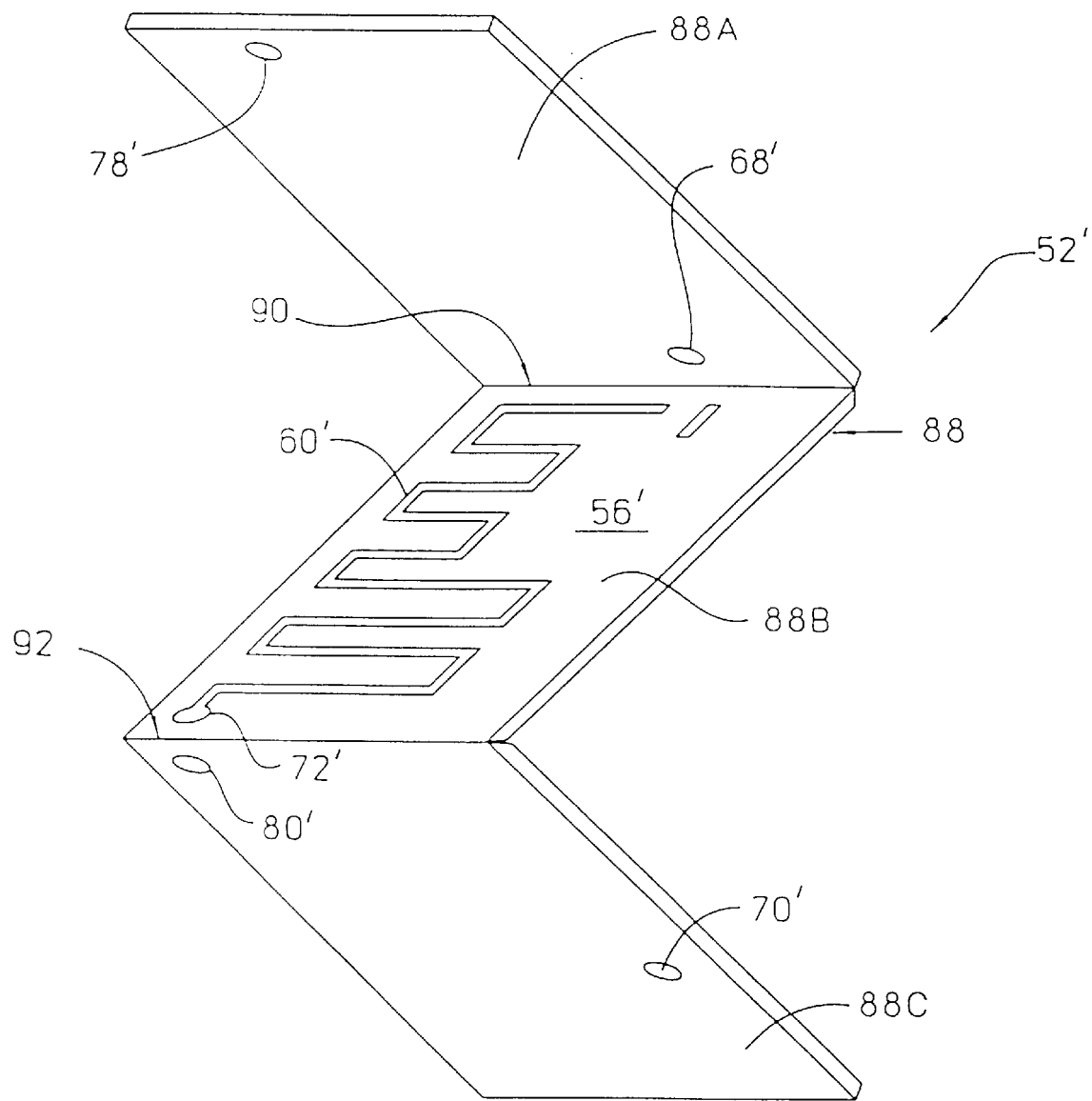
FIG. 8A is a pictorial representation of a first side of a preferred embodiment of the miniaturized column device of FIG. 7A which is constructed from a single flexible substrate.
Figure 8B:
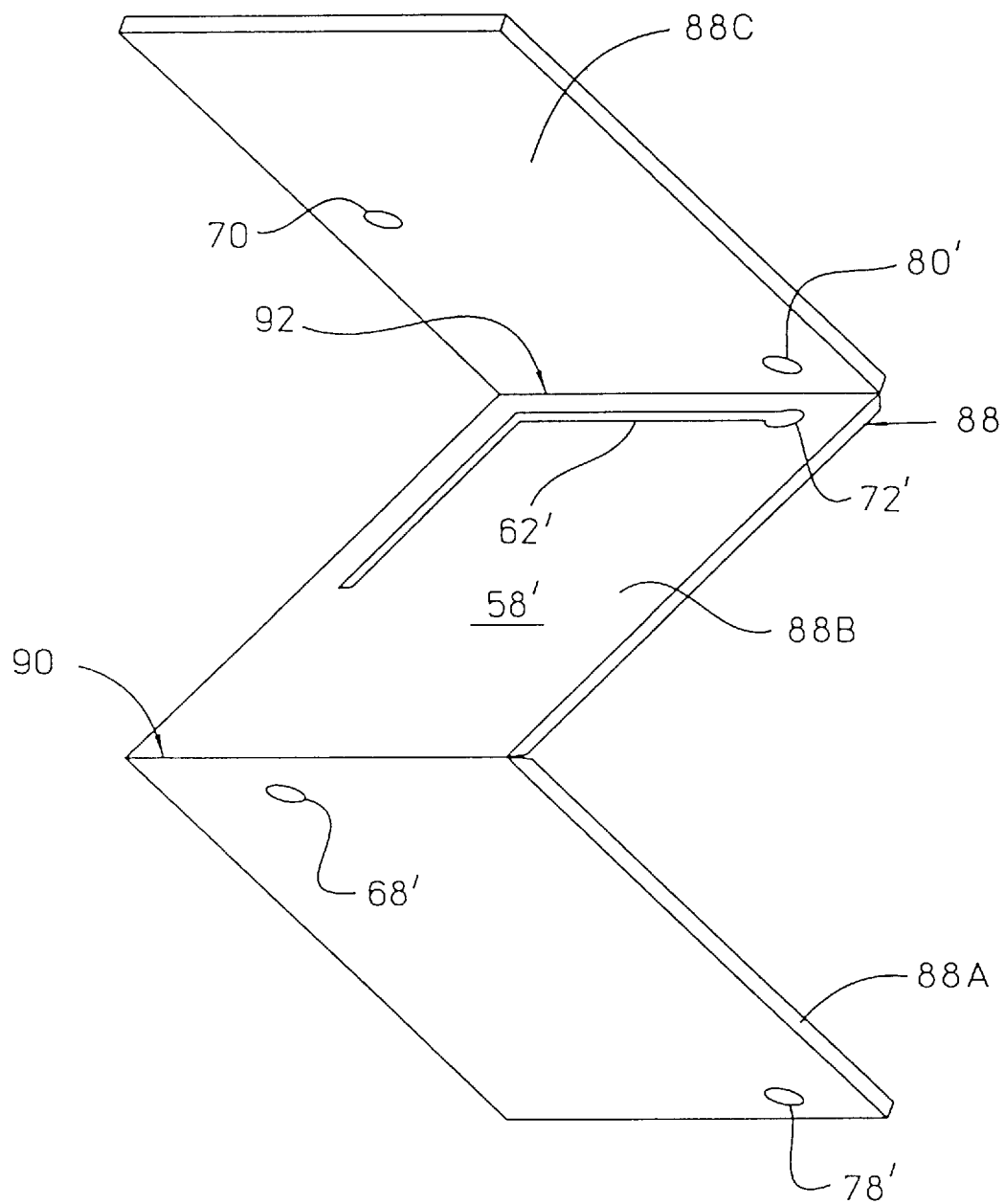
FIG. 8B is a pictorial representation of a second side of the column device of FIG. 8A.

Referring now to FIGS. 8A and 8B, a related embodiment of the invention is shown, comprising a miniaturized column device 52', wherein the column portion and the first and second cover plates are formed in a single, flexible substrate generally indicated at 88. The flexible substrate 88 thus comprises three distinct regions, a column portion 88B, having first and second substantially planar opposing surfaces 56' and 58', respectively, where the column portion is interposed between a first cover plate portion 88A and a second cover plate portion 88C. The first and second cover plate portions have at least one substantially planar surface. The first cover plate portion 88A and the column portion 88B are separated by at least one fold means 90 such that the first cover plate portion can be readily folded to overlie the first substantially planar surface 56' of the column portion 88B. The second cover plate portion 88C and the column portion 88B are likewise separated by at least one fold means 92 such that the second cover plate can be readily folded to overlie the second substantially planar surface 58' of the column portion 88B. In particularly preferred embodiments, each fold means 90 and 92 can comprise a row of spaced-apart perforations ablated in the flexible substrate, spaced-apart slot-like depressions or apertures ablated so as to extend only part way through the substrate, or the like. The perforations or depressions can have circular, diamond, hexagonal or other shapes that promote hinge formation along a predetermined straight line.

Thus, the miniaturized column device 52' is formed by laser ablating a first microchannel 60' in the first planar surface 56' of the column portion 88B, and a second microchannel 62' in the second planar surface 58' of the column portion. Each microchannel can be provided in a wide variety of geometries, configurations and aspect ratios. A first separation compartment is then formed by folding the flexible substrate 88 at the first fold means 90 such that the first cover plate portion 88A covers the first microchannel 60' to form an elongate separation compartment. A second separation compartment is then provided by folding the flexible substrate 88 at the second fold means 92 such that the second cover plate portion 88C covers the second microchannel 62' to form a separation compartment as described above. A conduit means 72', comprising a laser ablated aperture in the column portion 88B having an axis which is orthogonal to the first and second planar surfaces 56' and 58', communicates a distal end of the first microchannel 60' with a first end of the second microchannel 62' to form a single, extended separation compartment.

Further, an aperture 68', laser ablated in the first cover plate portion 88A, enables fluid communication with the first microchannel 60', and a second aperture 70', laser ablated in the second cover plate portion 88C, enables fluid communication with the second microchannel 62'. As described above, when the first and second apertures are used as an inlet and outlet port, respectively, a miniaturized column device is provided having a flow path extending along the combined length of the first and second microchannels.

Detection means can optionally be included in the device of FIGS. 8A and 8B. In one particular embodiment, a first aperture 78' can be laser ablated in the first cover plate portion 88A, and a second aperture 80' can likewise be formed in the second cover plate portion 88C, wherein the apertures are arranged to coaxially communicate with each other and communicate with the conduit means 72' when the flexible substrate 88 is hingably folded as described above to accurately align the apertures 78' and 80' with the conduit means 72'.

In yet further related aspects of the invention, optional micro-alignment means—formed either by laser ablation techniques or by other methods of fabricating shaped pieces well known in the art—are provided in the miniaturized column device 52'. More specifically, a plurality of corresponding laser-ablated apertures (not shown) can be provided in the column portion 88B and the first and second cover plate portions, 88A and 88C, respectively of the flexible substrate 88. The subject apertures are arranged such that coaxial alignment thereof enables the precise alignment of the column portion with one, or both of the cover plate portions to align various features such as the optional detection means with the ablated conduit. Such optional alignment can be effected using an external apparatus with means (such as pins) for cooperating with the coaxial apertures to maintain the components are portions in proper alignment with each other.

Accordingly, novel miniaturized column devices have been described which are laser ablated into a substrate other than silicon or silicon dioxide materials, and which avoid several major problems that have come to be associated with prior attempts at providing micro-column devices. The use of laser ablation techniques in the practice of the invention enables highly symmetrical and accurately defined micro-column devices to be fabricated in a wide class of polymeric and ceramic substrates to provide a variety of miniaturized liquid-phase analysis systems. Particularly, miniaturized columns are provided which have micro-capillary dimensions (ranging from 20–200 μm in diameter) and column detection path lengths of up to 1 mm or greater. This feature has not been attainable in prior attempts at miniaturization, such as in capillary electrophoresis, without substantial engineering of a device after capillary formation. Further, laser ablation of miniaturized columns in inert substrates such as polyimides avoids the problems encountered in prior devices formed in silicon or silicon dioxide-based materials. Such problems include the inherent chemical activity and pH instability of silicon and silicon dioxide-based substrates which limits the types of separations capable of being performed in those devices.

In the practice of the invention, miniaturized column devices can be formed by laser ablating a set of desired features in a selected substrate using a step-and-repeat process to form discrete units. In this regard, a wide variety of devices can be laser ablated according to the invention in condensation polymer substrates including polyimides, polyamides, poly-esters and poly-carbonates. Further, the invention can be practiced using either a laser ablation process or a LIGA process to form templates encompassing a set of desired features, whereby multiple copies of miniaturized columns can be mass-produced using injection molding techniques well known in the art. More particularly, multiple copies of the novel miniaturized columns can be formed herein by injection molding in substrates such as, but not limited to, the following substrates: polycarbonates; polyesters, including poly(ethylene terephthalate) and poly (butylene terephthalate); polyamides, (such as nylons); polyethers, including polyformaldehyde and poly(phenylene sulfide); polyimides, such as Kapton® and Upilex®; poly-olefin compounds, including ABS polymers, Kel-F copolymers, poly(methyl methacrylate), poly(styrene-butadiene) copolymers, poly(tetrafluoroethylene), poly (ethylene-vinyl acetate) copolymers, poly(N-vinylcarbazole) and polystyrene.

Laser ablation of microchannels in the surfaces of the above-described substrates has the added feature of enabling a wide variety of surface treatments to be applied to the microchannels before formation of the separation compartment. That is, the open configuration of laser-ablated microchannels produced using the method of the invention enables a number of surface treatments or modifications to be performed which are not possible in closed format constructions, such as in prior micro-capillaries. More specifically, laser ablation in condensation polymer substrates provides microchannels with surfaces featuring functional groups, such as carboxyl groups, hydroxyl groups and amine groups, thereby enabling chemical bonding of selected species to the surface of the subject microchannels using techniques well known in the art. Other surface treatments enabled by the open configuration of the instant devices include surface adsorptions, polymer graftings and thin film deposition of materials such as diamond or sapphire to microchannel surfaces using masking and deposition techniques and dynamic deactivation techniques well known in the art of liquid separations.

The ability to exert rigid computerized control over laser ablation processes enables extremely precise microstructure formation, which, in turn, enables the formation of miniaturized columns having features ablated in two substantially planar components wherein those components can be aligned to define a composite separation compartment of enhanced symmetry and axial alignment. Thus, in a further embodiment of the invention, miniaturized column devices are provided wherein laser ablation is used to create two component halves which, when folded or aligned with each other, define a single miniaturized column device.

Figure 10:
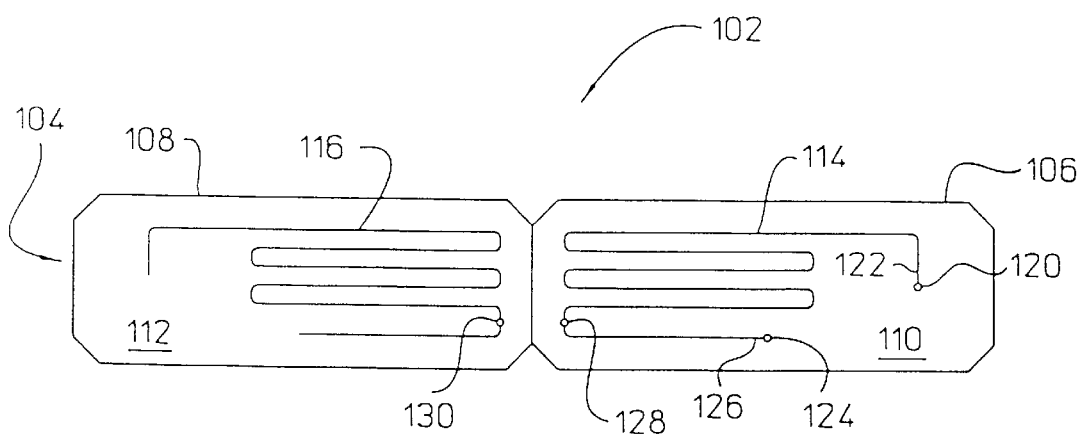
FIG. 10 is plan view of a miniaturized column device constructed under the invention having first and second component halves.

Referring now to FIG. 10, a miniaturized column for liquid phase analysis of a sample is generally indicated at 102. The miniaturized column 102 is formed by providing a support body 104 having first and second component halves indicated at 106 and 108 respectively. The support body can comprise a substantially planar substrate such as a polyimide film which is both laser ablatable and flexible so as to enable folding after ablation; however, the particular substrate selected is not considered to be limiting in the invention.

The first and second component halves, 106 and 108, each have substantially planar interior surfaces, indicated at 110 and 112 respectively, wherein miniaturized column features can be laser ablated. More particularly, a first microchannel pattern 114 is laser ablated in the first planar interior surface 110 and a second microchannel pattern 116 is laser ablated in the second planar interior surface 112. The first and second microchannel patterns are ablated in the support body 104 so as to substantially provide the mirror image of each other.

Figure 11:
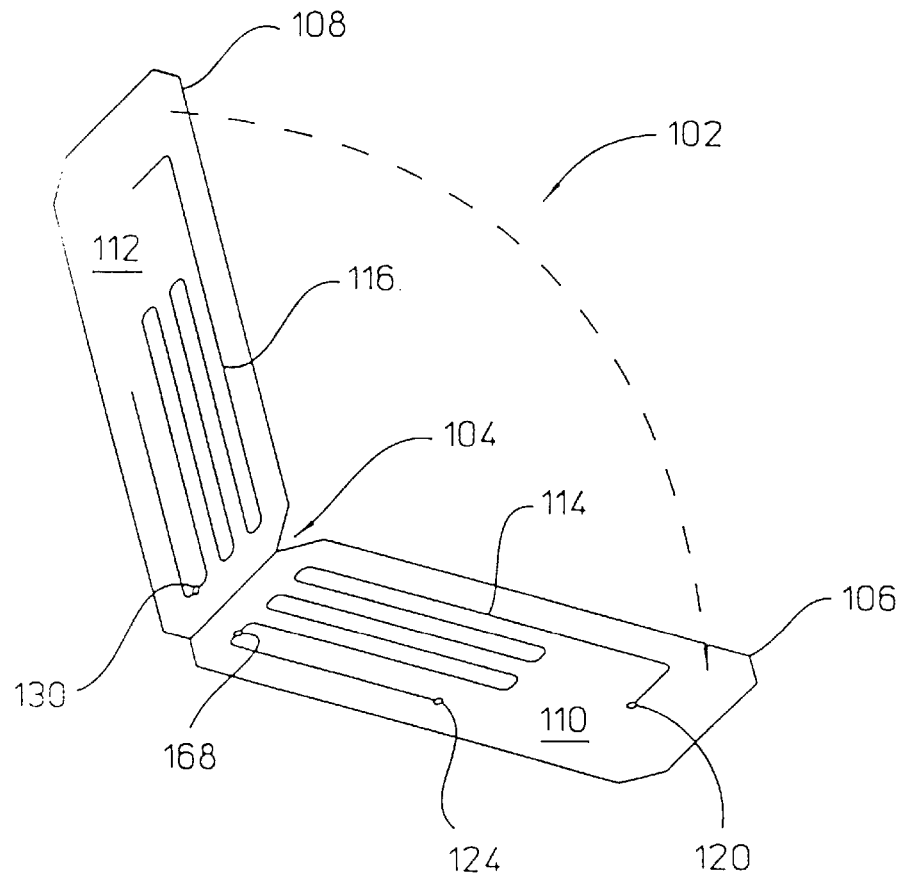
FIG. 11 is a pictorial representation of the column device of FIG. 10 showing the folding alignment of the component halves to form a single device.
Figure 12:
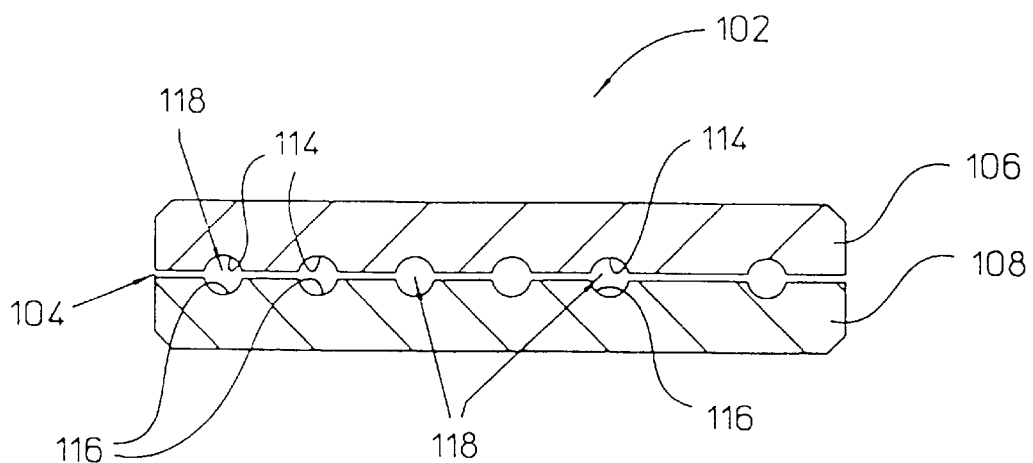
FIG. 12 is a cross-sectional axial view of the separation compartment formed by the alignment of the component halves in the device of FIG. 10.

Referring now to FIGS. 11 and 12, a separation compartment 118, comprising an elongate bore defined by the first and second microchannel patterns 114 and 116 can be formed by aligning (such as by folding) the first and second component halves 106 and 108 in facing abutment with each other. In the practice of the invention, the first and second component halves can be held in fixable alignment with one another to form a liquid-tight separation compartment using pressure sealing techniques, such as by application of tensioned force, or by use of adhesives well known in the art of liquid phase separation devices. In one particular embodiment, first and second microchannels 114 and 116 are provided having semi-circular cross-sections, whereby alignment of the component halves defines a separation compartment 118 having a highly symmetrical circular cross-section to enable enhanced fluid flow therethrough; however, as discussed above, a wide variety of microchannel geometries are also within the spirit of the invention.

In a further preferred embodiment of the invention, the support body 104 is formed from a polymer laminate substrate comprising a Kapton® film co-extruded with a thin layer of a thermal plastic form of polyimide referred to as KJ and available from DuPont (Wilmington, Del.). In this manner, the first and second component halves 106 and 108 can be heat sealed together, resulting in a liquid-tight weld that has the same chemical properties and, accordingly, the same mechanical, electrical and chemical stability, as the bulk Kapton® material.

Referring now to FIGS. 10–12, the miniaturized column device 102 further includes means for communicating associated external fluid containment means (not shown) with the separation compartment 118 to provide a liquid-phase separation device. More particularly, a plurality of apertures can be laser ablated in the support body 104, wherein the apertures extend from at least one exterior surface of the support body and communicate with at least one microchannel, said apertures permitting the passage of fluid therethrough. More particularly, an inlet port 120 can be laser ablated in the first component half 106 to communicate with a first end 122 of the first microchannel 114. In the same manner, an outlet port 124 can be ablated in the first component half to communicate with a second end 126 of the first microchannel 114.

In this manner, a liquid phase separation device is readily provided, having a flow path extending from the first end 122 of the microchannel 114 to the second end 126 thereof, by communicating fluids from an associated source (not shown) through the inlet port 120, passing the fluids through the separation compartment 118 formed by the alignment of microchannels 114 and 116, and allowing the fluids to exit the separation compartment via the outlet port 126. Thus, a wide variety of liquid phase analysis procedures can be carried out in the subject miniaturized column device using techniques well known in the art. Furthermore, various means for applying a motive force along the length of the separation compartment 118, such as a pressure differential or electric potential, can be readily interfaced to the column device via the inlet and outlet ports, or by interfacing with the separation compartment via additional apertures which can be ablated in the support body 104.

In particular preferred embodiments, the inlet port 120 can be formed such that a variety of external fluid and/or sample introduction means are readily interfaced with the miniaturized column device 102. As discussed above, such sample introduction means include external pressure injection, hydrodynamic injection or electrokinetic injection mechanisms.

Referring now to FIGS. 10 and 11, the miniaturized column device 102 can further include a detection means laser ablated in the support body 104. More particularly, a first aperture 128 is ablated in the first component half 106 to communicate with the first microchannel 114 at a point near the second end 126 thereof. A second aperture 130 is likewise formed in the second component half 108 to communicate with the second microchannel 116. In this manner, a wide variety of associated detection means can then be interfaced to the separation compartment 118 to detect separated analytes of interest passing therethrough, such as by connection of electrodes to the miniaturized column via the first and second apertures 128 and 130.

In yet a further preferred embodiment of the invention, an optical detection means is provided in the miniaturized column device 102. In this regard, first and second apertures 128 and 130 are ablated in the support body 104 such that when the component halves are aligned to form the separation compartment 118, the apertures are in coaxial alignment with each other, wherein the apertures have axes orthogonal to the plane of the support body. As will be readily appreciated by one of ordinary skill in the art, by providing transparent sheets (not shown)—disposed over the exterior of the support body 104 and covering the first and second apertures 128 and 130—a sample passing through the separation compartment 118 can be analyzed by interfacing spectrophotometric detection means with the sample through the transparent sheets using techniques well known in the art. The optical detection pathlength is substantially determined by the combined thickness of the first and second component halves 106 and 108. In this manner, an optical detection pathlength of up to 250 $\mu$m is readily provided by ablating the miniaturized column device in a 125 $\mu$m polymer film.

Accordingly, there have been described several preferred embodiments of a miniaturized column device formed according to the invention by laser ablating microstructures in component parts and aligning the components to form columns having enhanced symmetries. As described above, formation of the subject microchannels in the open configuration enables a wide variety of surface treatments and modifications to be applied to the interior surfaces of the channels before alignment of the components to provide the separation compartment. In this manner, a wide variety of liquid phase analysis techniques can be carried out in the composite separation compartments thus formed, including chromatographic, electrophoretic and electrochromatographic separations.

In yet a further embodiment of the invention, optional means are provided for the precise alignment of component support body halves, thereby ensuring accurate definition of a composite separation compartment formed thereby. More particularly, optional micro-alignment means are provided to enable enhanced alignment of laser-ablated component parts, such as the precise alignment of complementary microchannels with each other, detection apertures with microchannels, inlet and outlet ports with microchannels, detection apertures with further detection apertures, and the like.

Figure 13:
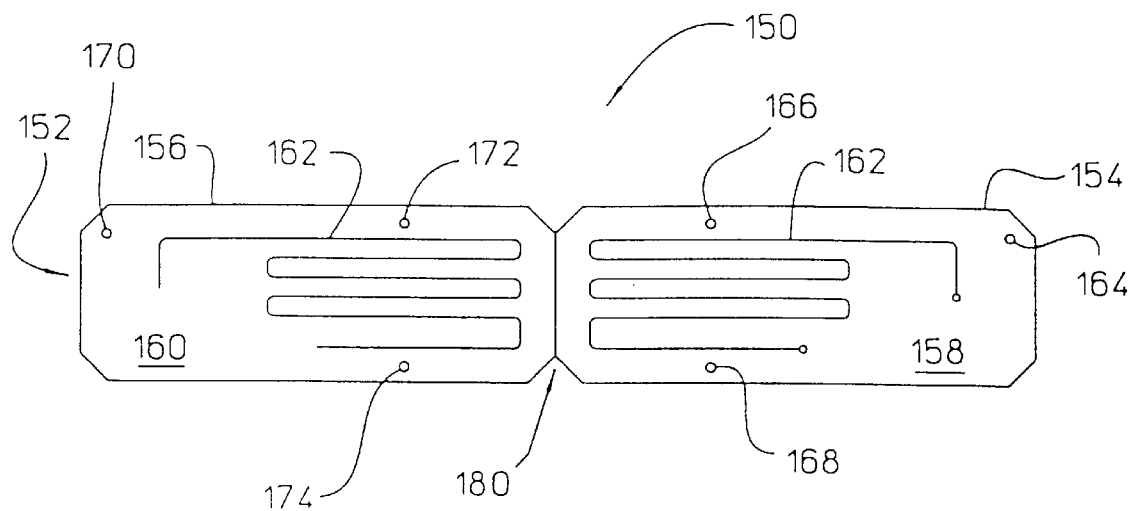
FIG. 13 is a plan view of a further preferred embodiment of the present invention having optional micro-alignment means on first and second component halves.
Figure 14:
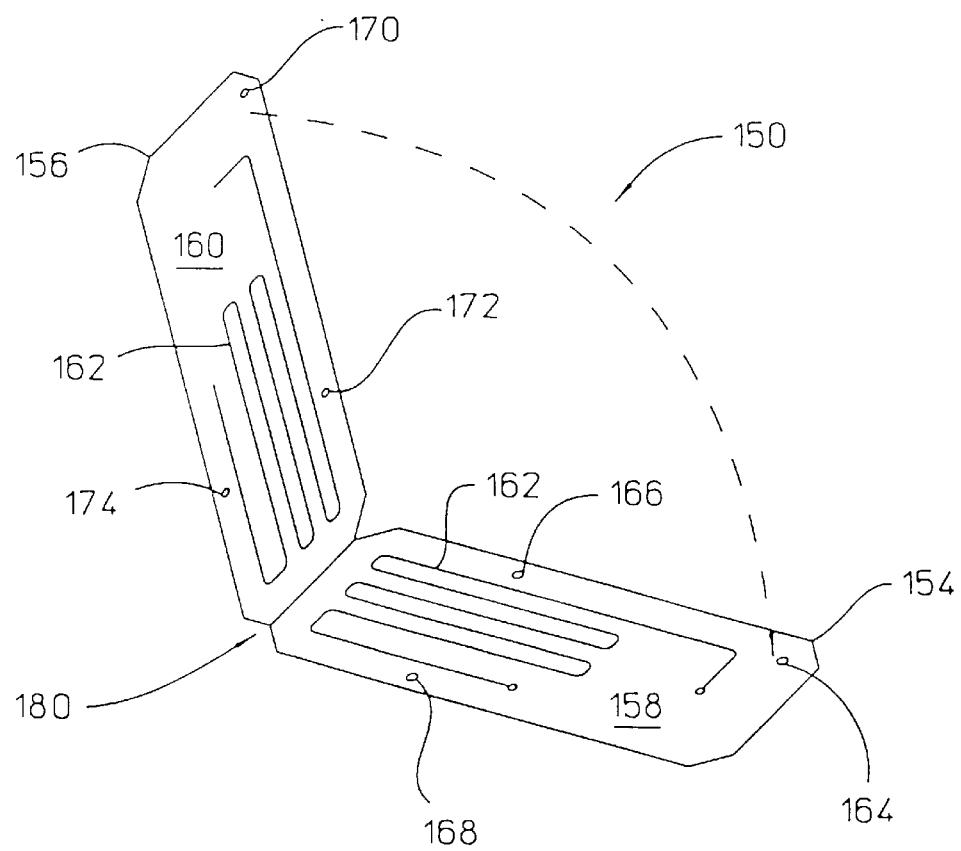
FIG. 14 is a pictorial representation of the column device of FIG. 13 showing the micro-alignment of the component halves.

Referring now to FIGS. 13 and 14, a miniaturized column device constructed according to the present invention is generally indicated at 150, wherein the device is formed in a single flexible substrate 152. The column device comprises first and second support body halves, indicated at 154 and 156 respectively, each half comprising a substantially planar interior surface indicated at 158 and 160 respectively. The interior surfaces have laser-ablated microstructures formed therein, generally indicated at 162, wherein the microstructures are arranged to provide the mirror image of each other in the same manner as described above.

More particularly, the accurate alignment of the component parts is effected by forming a miniaturized column device in a flexible substrate 152 having at least one fold means, generally indicated at 180, such that the first body half 154 can be folded to overlie the second body half 156. The fold means 180 can comprise a row of spaced-apart perforations ablated in the substrate 152, spaced-apart slot-like depressions or apertures ablated so as to extend only part way through the substrate, or the like. The perforations or depressions can have circular, diamond, hexagonal or other shapes that promote hinge formation along a predetermined straight line.

Accordingly, in the practice of the invention, the fold means 180 allows the first and second support body halves 154 and 156 to hingably fold upon each other to precisely align various composite features that are defined by the microstructures ablated in the first and second planar interior surfaces 158 and 160.

In a related embodiment, optionally micro-alignment means are provided in the first and/or second planar interior surfaces 158 and 160. The micro-alignment means are formed either by laser ablation or by other methods of fabricating shaped pieces well known in the art. More specifically, a plurality of laser-ablated apertures (not shown) can be provided in the first and second support body halves 154 and 156, wherein the apertures are arranged such that the coaxial alignment thereof effects the precise alignment of the support body halves to define composite features, such as an ablated elongate bore. Such alignment can be maintained using an external apparatus with means (such as pins) for cooperating with the coaxial apertures to support the body halves in proper alignment with one another.

Referring to FIGS. 13 and 14, in yet another particular embodiment of the invention, micro-alignment means can be formed in the first and second support body halves 154 and 156 using fabrication techniques well known in the art, e.g., molding or the like. In this manner, a plurality of projections, indicated at 164, 166 and 168, can be formed in the first support body half 154. A plurality of depressions, indicated at 170, 172 and 174, can be formed in the second support body half 156.

In this particular configuration, the micro-alignment means are designed to form corresponding (mating) structures with each other, whereby projection 164 mates with depression 170, projection 166 mates with depression 172, and projection 168 mates with depression 174 when the support body halves are aligned in facing abutment with each other. In this manner, positive and precise alignment of support body halves 154 and 156 is enabled, thereby accurately defining composite features defined by the laser-ablated microstructures 162.

As will be readily apparent to one of ordinary skill in the art after reading this specification, a wide variety of corresponding micro-alignment features can be formed in the subject miniaturized column devices without departing from the spirit of the instant invention. These additional features include any combination of holes and/or corresponding structures such as grooves and ridges in the component parts where the features cooperate to enable precise alignment of the component body parts.

Figure 15:
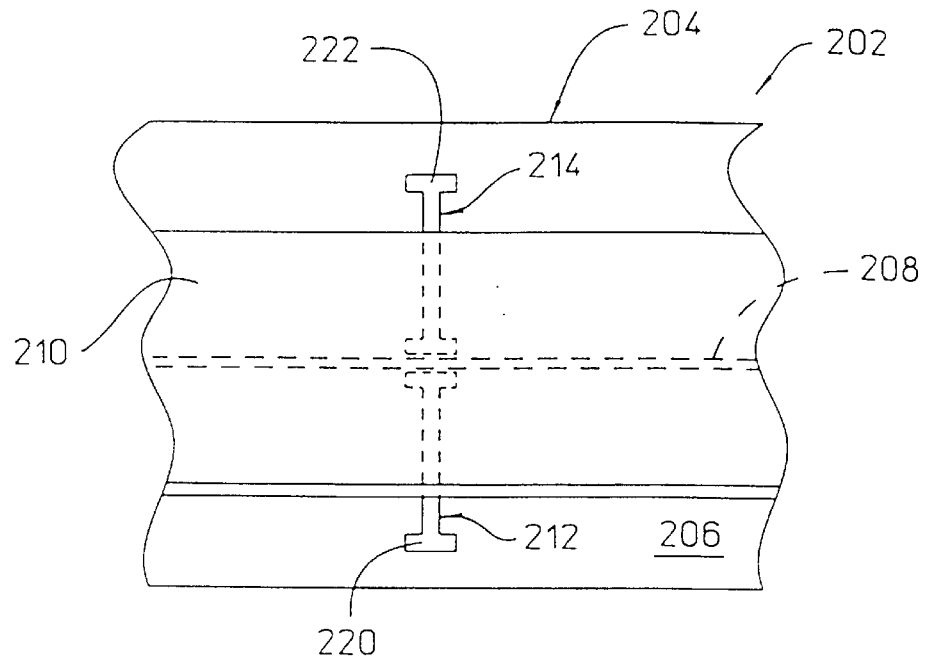
FIG. 15 is a plan view of the top surface of a miniaturized column device including electrical communication path detection means arranged opposite each other relative to a separation compartment.

In yet a further aspect of the invention, an electrical detection means is provided that is capable of detecting changes in the electrical properties of a liquid sample passing through the separation compartment of any of the miniaturized column device embodiments of the invention. Referring to FIG. 15, a miniaturized column device constructed according to the invention is generally indicated at 202. The device is formed in an appropriate substrate 204 which has at least one substantially planar surface, indicated at 206. A microchannel 208 is formed in the substrate 206 as described above using laser ablation techniques. Thus, a cover plate 210 arranged over the microchannel 208 forms a separation compartment. The cover plate can be formed from any suitable substrate such as polyimide, where the selection is limited only by the avoidance of undesirable separation surfaces such as silicon or silicon dioxide materials.

Figure 16:
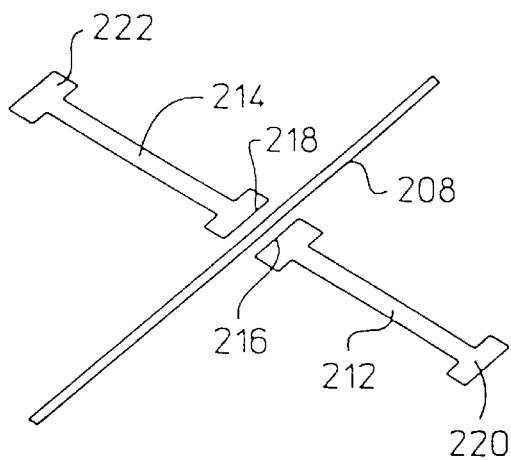
FIG. 16 is a pictorial representation of the electrode means of FIG. 15.
Figure 17:
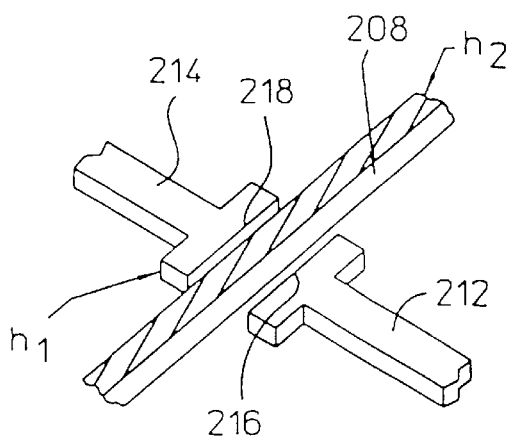
FIG. 17 is a pictorial representation of the electrode means depicted in FIG. 16 showing a preferred height feature thereof.

Referring now to FIGS. 15–17, a plurality of detection means, comprising first and second electrical communication paths 212 and 214, respectively, are arranged opposite each other relative to the microchannel 208. More particularly, a first end 216 of communication path 212 is arranged alongside and directly adjacent to a first side of the microchannel 208. A first end 218 of communication path 214 is arranged alongside and directly adjacent to a second side of the microchannel such that the ends 216 and 218 form a detection path interrupted by the microchannel. The communication path ends 216 and 218 have no direct contact with the microchannel. More particularly, there is at least about several $\mu$m of substrate 204 between the ends (216 and 218) and the microchannel 208. In this manner, there is no direct contact of the communication paths with the sample passing through the separation compartment. This arrangement avoids galvanic contact of the communication paths with the sample and associated electrolysis leading to gas bubble generation, and ensures that the communication paths remain stable and provide accurate, reproducible measurements.

Referring still to FIGS. 15–17, connection of the subject detection means with an appropriate associated signal source, such as an AC signal source (not shown), is effected through exposed contact points 220 and 222, which are arranged at a second end of communication paths 212 and 214, respectively. In this manner, communication paths 212 and 214 are used to provide an antenna circuit which is capable of generating an electric field encompassing the separation compartment, whereby a phase shift due to changes in the conductance or permittivity of a streaming liquid sample passing through the compartment provides a linear, detectable signal to an associated impedance meter or any other appropriate permittivity detector. More particularly, the communication paths 212 and 214 can be used as electrode antennae to generate an electric field, wherein the antennae form part of a resonance circuit. The amplitude of an oscillating frequency in the subject resonance circuit will be proportional to the conductivity of the contents of the separation compartment. Thus, a constant phase lag can be generated by varying the frequency of an oscillating signal transmitted by the antennae. The phase lag will fluctuate in response to changes in the conductivity, permittivity, or both, of the contents of the separation compartment streaming through the electric field which is in turn fed back to vary the frequency in the antennae to compensate for the shift in the phase lag, thereby providing a detectable signal.

In one particular embodiment, communication paths 212 and 214 are formed on the substrate 204 by sputtering deposition techniques well known in the art. In a related embodiment, the communication paths can be formed in copper-polymer laminate substrates, wherein the paths are formed using etching, ablation or micromachining techniques well known in the art. In one particularly preferred embodiment, communication paths 212 and 214 can be formed using laser ablation techniques, whereby the path configuration is laser-ablated in the substrate to form depressions which can subsequently be filled with an appropriate conductive material. The electric field strength of antennae circuit formed by the path configuration is controlled by the voltage applied thereto, and the distance between the antennae. Referring particularly to FIG. 17, such techniques allow the formation of conductive paths in any laser-ablatable configuration, and further readily enable the formation of paths having a height $h_1$ which is co-extensive with the height $h_2$ of the microchannel 208. In this regard, the strength of a generated electric signal can be controlled by variations in the height and the length of the opposing communication path ends 216 and 218.

Figure 18:
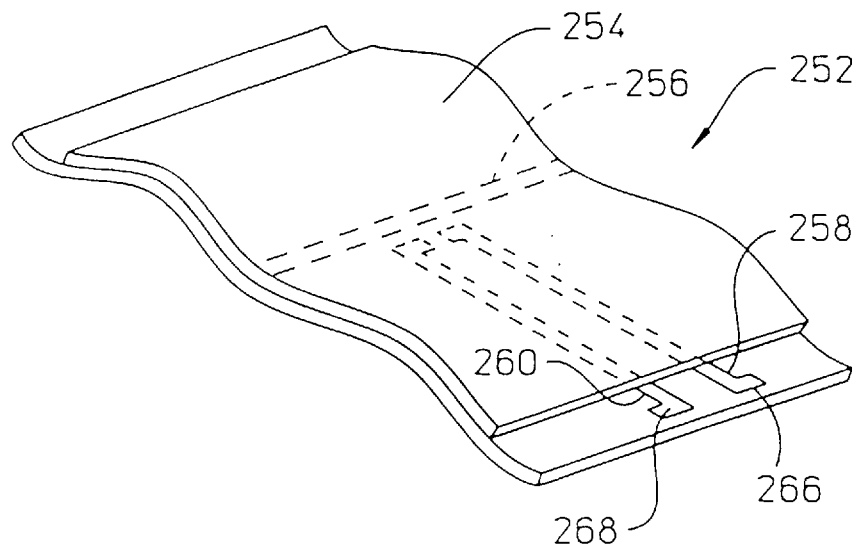
FIG. 18 is a pictorial representation of the top surface of a miniaturized column device including electrode means arranged substantially parallel relative each other on a first side of a separation compartment.
Figure 19:
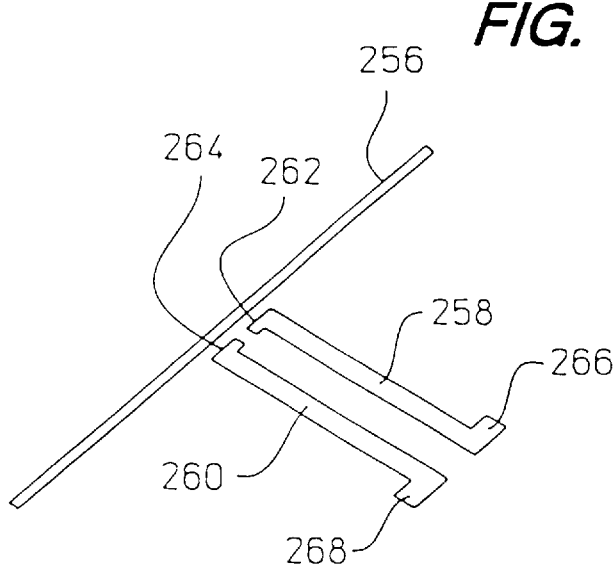
FIG. 19 is a pictorial representation of the electrode means of FIG. 18.
Figure 20:
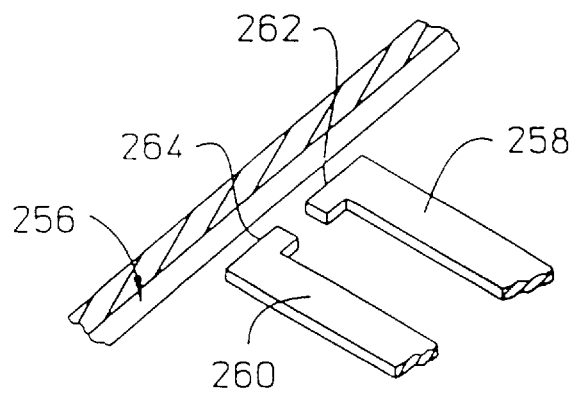
FIG. 20 is a pictorial representation of the electrode means depicted in FIG. 19 showing a preferred height feature thereof.

A number of additional configurations of electrical detection means can be provided in the above-described devices. Referring to FIGS. 18–20, a further embodiment of the invention, comprising a miniaturized column device, is generally indicated at 252, having a cover plate 254 arranged over a microchannel 256 to form a separation compartment. A plurality of detection means, comprising first and second electrical communication paths 258 and 260, respectively, are arranged in spaced-apart relation to each other in the longitudinal direction along a first side of microchannel 256.

Referring particularly to FIGS. 19 and 20, communication paths 258 and 260 have first ends 262 and 264, respectively, which are arranged directly adjacent to the microchannel 256; however, ends 262 and 264 are not in direct contact with the microchannel as described above. Exposed contact points 266 and 268, respectively arranged at second ends of communication paths 258 and 260, are available for connection to an associated signal generator. In this manner, communication paths 212 and 214 can be used herein to provide an antenna circuit which is capable of generating an electric field encompassing the separation compartment, whereby a phase shift produced by changes in the conductance or permittivity of a streaming liquid sample passing through the compartment provides a detectable signal as described above. Referring particularly to FIG. 20, communication paths 258 and 260 can be formed using laser ablation techniques, such that the height $h_3$ of path ends 262 and 264 is co-extensive with the height $h_4$ of microchannel 256 to provide enhanced signal strength.

Figure 21:
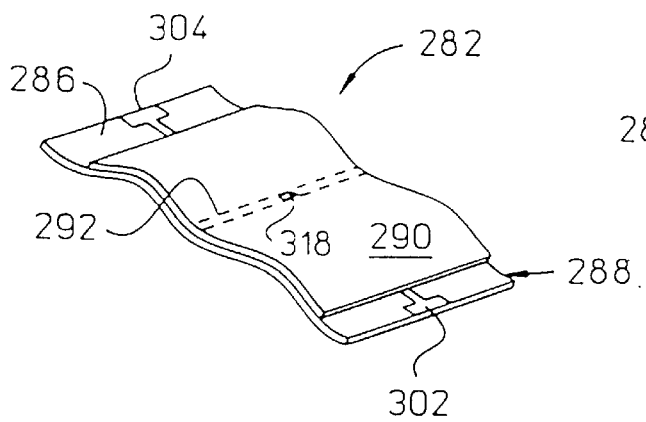
FIG. 21 is a pictorial representation of the top surface of a miniaturized column device including a plurality of serially arranged annular electrode coils.
Figure 22:
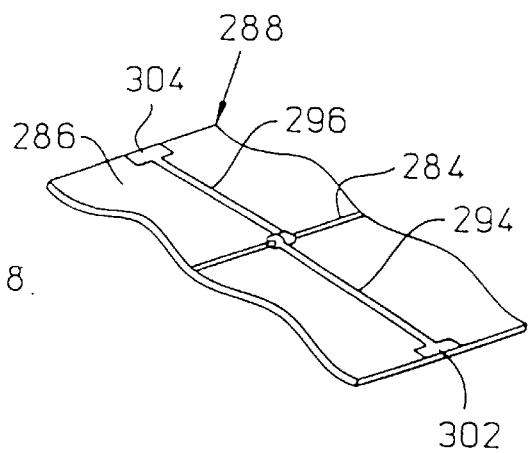
FIG. 22 is a pictorial representation similar to FIG. 21 wherein the cover plate is removed to expose the annular electrode coils.
Figure 24:
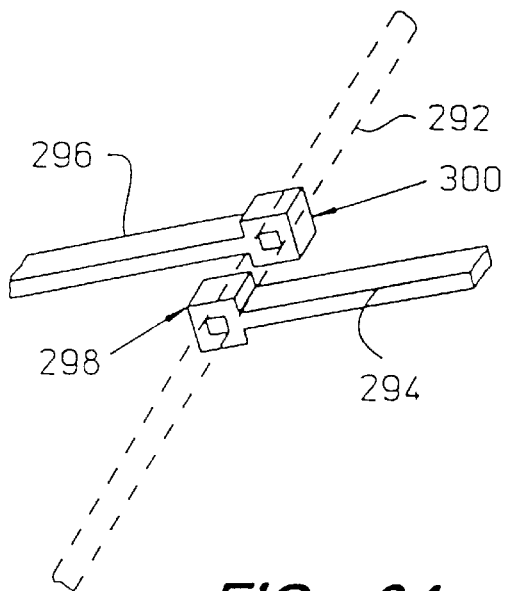
FIG. 24 is a pictorial representation of the annular electrodes of FIG. 22 illustrating the coaxial-arrangement thereof about a separation compartment.

In yet a further related embodiment, an electrical detection configuration is provided comprising a plurality of serially arranged coils arranged in coaxial relation about the separation compartment. In one embodiment, a plurality of serially arranged annular coils are provided to approximate an electrical coil detection configuration. Referring to FIGS. 21 and 22, a miniaturized column device 282 is depicted, having a microchannel 284 laser-ablated in a first substantially planar surface 286 of an appropriate substrate 288. The microchannel 284, in combination with a cover plate 290, forms a separation compartment 292 as described above. Referring particularly to FIGS. 22 and 24, a plurality of detection means, comprising first 294 and second 296 communication paths, are provided, having first and second annular coil portions 298 and 300, respectively, that are arranged in coaxial relation about the separation compartment 292 and in spaced-apart relation to each other in the longitudinal direction along the compartment. Exposed contact points 302 and 304, arranged at distal ends of communication paths 294 and 296, respectively, allow connection of the subject detection means with an appropriate signal source.

In this manner, electrical detection can be effected using techniques well known in the art. More particularly, a magnetic field can be generated in the core of a first annular coil portion, e.g., 298. A part of the induced electrical field provided by that magnetic field travels along the separation compartment toward the second annular coil portion 300. The second coil 300 is capable of detecting and measuring the electrical field. Accordingly, a phase shift produced by changes in the conductance or permittivity of a streaming liquid sample passing through the compartment provides a detectable signal as described above.

Figure 23:
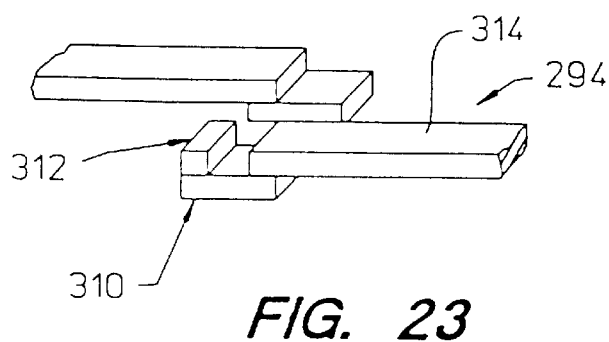
FIG. 23 is a pictorial representation demonstrating a preferred method of forming the electrodes of FIG. 22.
Figure 25:
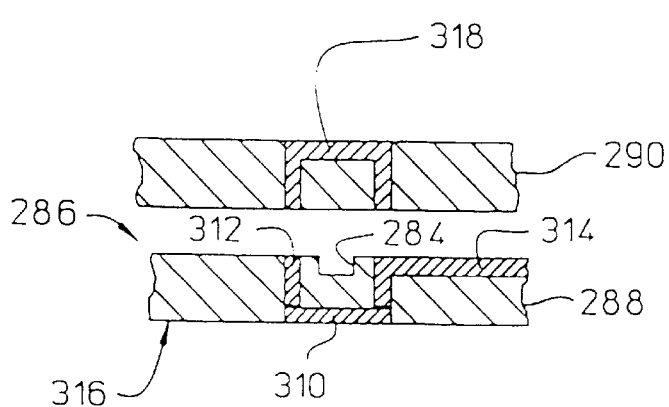
FIG. 25 is a cross-sectional view of an annular electrode coil from FIG. 22.

Communication paths 294 and 296 can be formed herein using any suitable method, including sputtering or other depositions, laser ablation, etching or micromachining techniques. In one particular embodiment, the annular coil configuration of communication path 294 can be formed as a composite structure. Referring to FIGS. 21, 23 and 25, a first portion of the annular coil configuration, indicated at 310, is provided by a conductive strip formed on a second planar surface 316 of substrate 288. The first portion 310 is thus arranged below microchannel 284. Second and third portions, 312 and 314, are formed by laser-ablation, wherein depressions are ablated in substrate 288 to communicate with first conductive portion 310, which depressions are subsequently filled-in with a suitable conductive material. Portions 312 and 314 are thus arranged in opposing relation to each other on first and second sides, respectively, of microchannel 284.

In this manner, a substantially U-shaped configuration is provided which surrounds the microchannel without coming into direct contact with the interior of the channel. The composite annular coil configuration is completed by forming a similar structure in cover plate 290, comprising a complementary U-shaped conductive portion 318 that is disposed so as to contact portions 312 and 314 when cover plate 290 is arranged over microchannel 284 to form the separation compartment as described above.

In a further aspect of the invention, a number of further detection configurations are provided, wherein integrated lightguides are employed to provide enhanced detection capabilities to the subject devices. In this regard, each of the miniaturized column device embodiments of the present invention can include means for employing one or more optional lightguide means.

More particularly, referring to FIG. 1A, a detection means comprising a single aperture 36 formed in cover plate 12 and communicating with separation compartment 14 will readily accept a lightguide means (not shown), such as an optical fiber, integrated lens configuration, or the like. In one particular embodiment, the lightguide means can comprise an optical fiber that is selected to have substantially the same dimensions as the aperture 36, whereby interface of the optical fiber with the aperture to communicate with the separation compartment provides a liquid-tight seal. The optical fiber can be configured so as to transmit a fluorescent excitation wavelength into the separation compartment 14, and to receive a fluorescent emission signal therefrom. In this manner, fluorescence detection techniques can be carried out using methods that are well known in the art.

Referring still to FIG. 1A, a further detection means configuration—comprising aperture 36 which is coaxially aligned with a second aperture 34 formed in substrate 4—provides an optical detection path. The optical detection path thus formed allows detection of separated analytes passing through separation compartment 14 via transmission of radiation orthogonal to the major axis of the separation compartment. Thus, a plurality of optional lightguide means, such as optical fibers and/or integrated lens means, can be readily interfaced with apertures 34 and 36 to communicate with the separation compartment 14 as previously described. In one particular embodiment, a first such optical fiber can be employed for sample illumination, and a second for light collection to enable near IR or UV/Vis optical detection of separated analytes passing through the separation compartment.

In further related embodiments, each of the column device embodiments of the present invention which include either a single aperture communicating with a separation compartment, or a plurality of coaxially aligned apertures communicating with a separation compartment and forming an optical detection path, can accommodate one or more optional lightguide means as just described.

Referring now to FIG. 26, yet a further related embodiment of the invention is shown, comprising a miniaturized column device generally indicated at 352. The device is formed from a first substrate portion 354, having a substantially planar surface 356 with a first microchannel 358 laser-ablated therein. The column device further includes a second substrate portion 360, having a substantially planar surface 362 with a second microchannel 364 laser-ablated therein. The second microchannel 364 is arranged to provide the mirror image of the first microchannel 358 when the first and second substantially planar surfaces 356 and 362 are arranged in facing abutment with each other to form a separation compartment as described above.

The device 352 further comprises a detection means formed from a laser-ablated groove set. More particularly, a first groove 366 is laser-ablated in the first planar surface 356 to communicate with the first microchannel 358. A second, complementary laser-ablated groove 368—which communicates with the second microchannel 364—is arranged in the second planar surface 362 to provide the mirror image of the first groove 366. In this manner, a detection path communicating with the separation compartment is provided. The detection path comprises a compartment that is formed from the complementary groove set when the first and second substantially planar surfaces 356 and 362 are arranged in facing abutment with each other.

Referring now to FIGS. 26 and 27, the detection path is configured to readily accept an associated lightguide means. Thus lightguide means 370, comprising an optical fiber, integrated lens configuration, or like means can be disposed within the detection path to communicate with the separation compartment. In one particular embodiment, lightguide means 370 comprises an optical fiber that is selected to have substantially the same dimensions as the compartment formed by the complementary groove set 366 and 368, whereby insertion of the optical fiber within the compartment provides a liquid-tight seal. The lightguide means 370 can thus be configured so as to transmit a fluorescent excitation wavelength into the separation compartment, and to receive a fluorescent emission signal therefrom as described above.

Referring now to FIG. 28, a related embodiment of the invention is shown comprising a miniaturized column device generally indicated at 382. The device is formed in a selected substrate 384 having a substantially planar surface 386. A microchannel 388 is laser-ablated in the planar surface 386 which is in communication with first and second laser-ablated grooves, indicated at 390 and 392, respectively. The first and second grooves are arranged opposite each other relative to the microchannel 388, thereby forming a detection path when cover plate 394 is arranged over the planar surface 386 to form a separation compartment as previously described.

Referring now to FIGS. 28 and 29, the optical detection path thus formed allows detection of separated analytes passing through the separation compartment via transmission of radiation orthogonal to the major axis of the separation compartment. Thus, first and second lightguide means, respectively indicated at 394 and 396, and comprising optical fibers, integrated lens means or the like, can be readily disposed within grooves 390 and 392 to communicate with the separation compartment as previously described. In one particular embodiment, a first optical fiber 394 can be employed for sample illumination, and a second fiber 396 for light collection to enable near IR or UV/Vis optical detection of separated analytes passing through the separation compartment.

Figure 30:
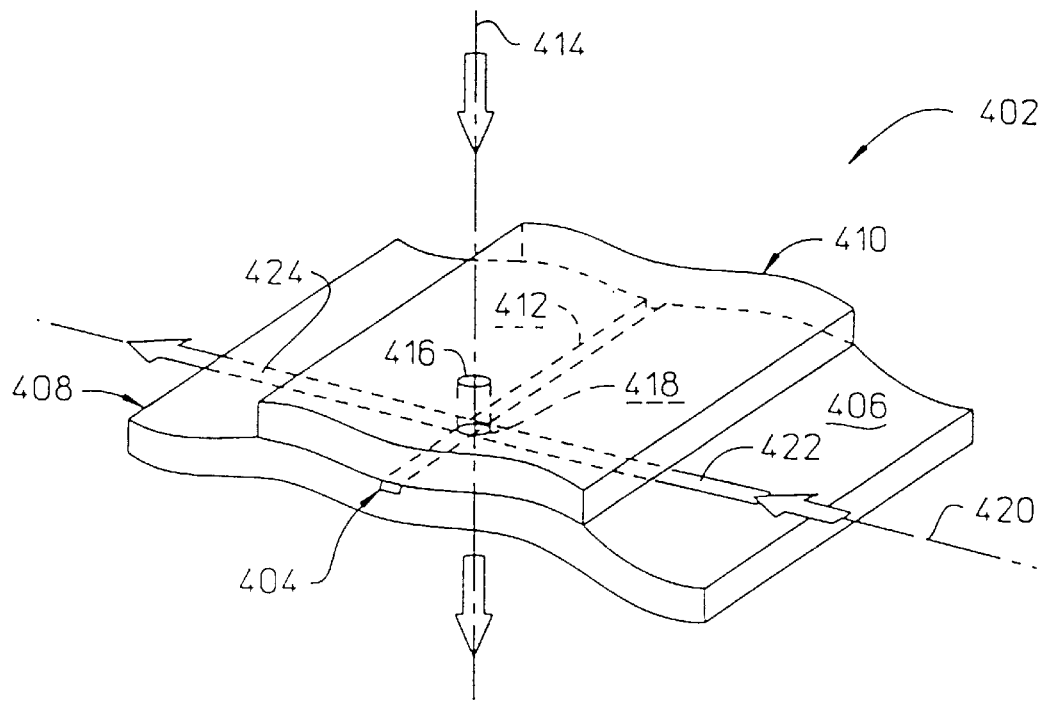
FIG. 30 is a pictorial representation of a miniaturized column device having a detection intersection formed by two orthogonal detection paths.

In a further aspect of the invention, miniaturized column devices formed according to the invention are provided having a plurality of detection means that converge at a particular location in the separation compartment. Referring to FIG. 30, one such device is generally indicated at 402. The column device comprises a laser-ablated microchannel 404 formed in a substantially planar surface 406 of a suitable substrate 408. Microchannel 404, in combination with cover plate 410 provides an elongate separation compartment 412. A first detection path, generally indicated at 414, is formed by the coaxial alignment of aperture 416—which is laser-ablated in cover plate 410 and arranged to communicate with separation compartment 412—and aperture 418, which is laser-ablated in substrate 408 to communicate with the separation compartment 412.

A second detection path, generally indicated at 420, is provided by first and second laser-ablated grooves, indicated at 422 and 424, respectively. The grooves are formed in planar surface 406 to communicate with the separation compartment 412 at first and second opposing sides thereof. In this manner, first and second grooves 422 and 424 are arranged opposite each other relative to the separation compartment 412 and form a second detection path when cover plate 410 is arranged over planar surface 406 to provide the separation compartment as previously described.

The first and second detection paths, 414 and 420, provide two mutually perpendicular optical axes which intersect within the separation compartment, wherein those axes are also orthogonal to the major axis of the separation compartment 412. Thus, a wide variety of simultaneous detection techniques can be carried out at the intersection of detection paths within the separation compartment.

In one particular embodiment, a first transparent sheet (not shown) can be arranged over aperture 416, and a second transparent sheet (not shown) can likewise be arranged over aperture 418 wherein said transparent sheets, in combination with the first detection path 414 form an optical detection path. In another embodiment, first and second lightguide means (not shown) can be interfaced with first and second apertures 416 and 418 to communicate with the separation compartment 412. As described above, such lightguides can comprise optical fibers that are capable of sample illumination and light collection to enable near IR or UV/Vis optical detection of separated analytes passing through the separation compartment.

In the above-described devices, the second detection path 420 can readily accommodate optional lightguide means to provide simultaneous optical detection, electrode pairs to provide simultaneous electrochemical detection, or communication paths to provide for simultaneous electrical detection, each of which detection configurations has been previously described.

Figure 31:
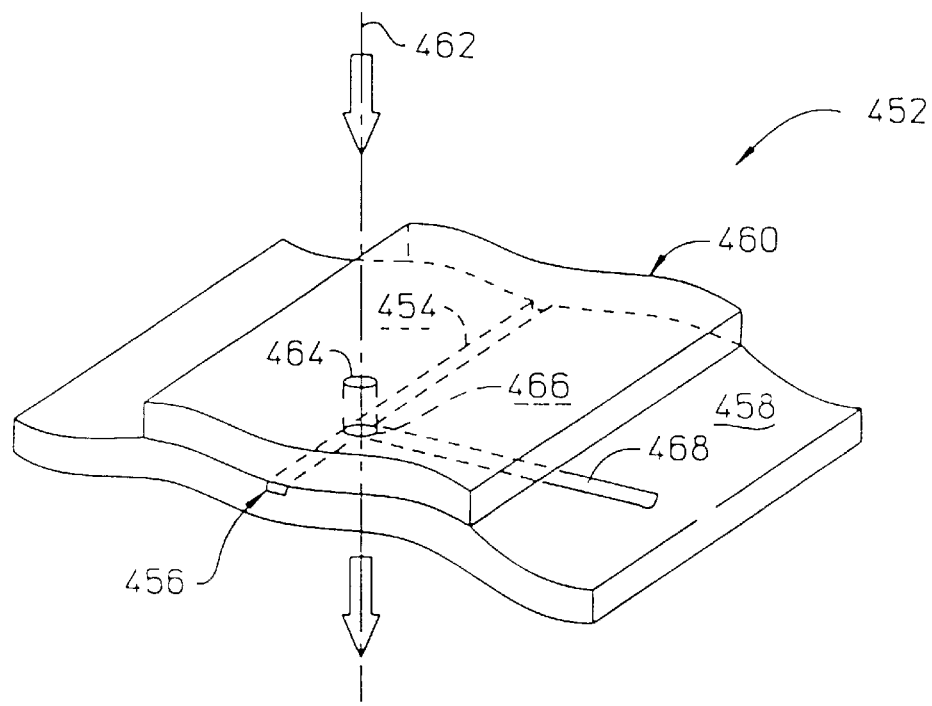
FIG. 31 is a pictorial representation of a miniaturized column device having a detection intersection formed by a detection path and a further detection means arranged in orthogonal relation to each other.

In FIG. 31, yet a further related embodiment is shown, comprising a miniaturized column device generally indicated at 452. The device comprises a separation compartment 454 formed from a laser-ablated microchannel 456 in a planar surface of a suitable substrate 458 and a cover plate 460. A first detection means comprising a detection path 462 is formed by the coaxial alignment of aperture 464 in cover plate 460 and aperture 466 in substrate 458 wherein each said aperture communicates with the separation compartment 454 as described above. A further detection means is formed from a laser-ablated groove 468 in substrate 458 which communicates with the separation compartment at substantially the same point that detection path 462 communicates with the separation compartment to provide a detection intersection.

Thus, first and second transparent sheets can be arranged over apertures 464 and 466, or lightguide means can be interfaced with said apertures to form an optical detection path from detection path 462 as previously described. Such arrangements allow detection techniques such as near IR or UV/Vis to be used in the detection of separated analytes passing through the separation compartment 454.

The further detection means is configured to readily accept an associated lightguide means. Thus, a lightguide means (not shown), comprising an optical fiber, integrated lens configuration, or like means, can be disposed within laser-ablated groove 468 to communicate with the separation compartment. In one particular embodiment, the lightguide means comprises an optical fiber that is configured to transmit a fluorescent excitation wavelength into the separation compartment, and to receive a fluorescent emission signal therefrom as described above. The lightguide means can also be configured to only receive light emission (e.g., fluorescence) in detections wherein excitation is performed through aperture 466.

Further, while the present invention has been described with reference to specific preferred embodiments, it is understood that the description and examples included herein are intended to illustrate and not limit the scope of the invention, which is defined by the scope of the appended claims.

We claim:

1. A method of forming a microchannel device, comprising the steps of:
    (a) providing a first substrate having a substantially planar surface;
    (b) forming by laser ablation a microchannel in the planer surface of the first substrate substantially parallel to the planar surface;
    (c) providing a second substrate having a substantially planar surface and miniaturized feature in that substantially planar surface;
    (d) deriving a first plate from the first substrate and deriving a second plate from the second substrate, the first plate having a planar surface and a microchannel corresponding to the planar surface and microchannel of the first substrate, and the second plate having a planar surface and miniaturized feature corresponding to the planar surface and the miniaturized feature of the second substrate; and
    (e) aligning two or more plates, including: aligning the first plate and the second plate such that the planar surface of the first plate and the planar surface of the second plate are in facing abutment and the miniaturized feature of the second plate is aligned with the microchannel of the first plate, thereby providing a miniaturized column device with a microcompartment including a microchannel.

2. The method according to claim 1 further comprising laser ablating the second substrate to form the miniaturized feature to include a microchannel.

3. The method according to claim 2 further comprising aligning the first plate with the second plate in facing abutment with each other, thereby aligning the microchannels to provide a miniaturized column device.

4. The method according to claim 1 wherein the first plate is the first substrate having a microchannel thereon.

5. The method according to claim 1 wherein the first plate is the first substrate having microchannels thereon and the second plate is the second substrate having miniaturized feature thereon.

6. The method according to claim 1 wherein the first plate is derived from the first substrate by using the first plate as a template in a molding process.

7. The method according to claim 1 further comprising laser-ablating apertures on the first substrate or the second substrate for providing detection means in the first plate or the second plate.

8. The method according to claim 1 further comprising aligning at least three plates each of which has miniaturized features derived from substrates having corresponding miniaturized features, the three plates including the first plate and the second plate.

9. The method according to claim 8 wherein at least two surfaces of the at least three plates have a microchannel.

10. The method according to claim 1 further comprising laser ablating at least two substrates to form microchannels thereon and deriving from the at least two substrates at least two plates each having a microchannel on a planar surface.

11. The method according to claim 10 further comprising laser ablating the at least two substrates such that the microchannel formed on each substrate is a mirror image of the microchannel of another of the at least two substrates.

12. The method according to claim 1 wherein the first substrate is a material other than silicon or silicon dioxide.

13. The method according to claim 12 wherein the first substrate is a polymeric substrate.

14. The method according to claim 12 wherein the first substrate is a ceramic substrate.

15. The method according to claim 1 further comprising providing a fold means connecting at least the first plate and the second plate, the fold means being formed by a process comprising laser ablating a row of spaced-apart perforations in a connecting material connecting the first plate and the second plate.

16. The method according to claim 1 further comprising providing corresponding projections and depressions on the planar surfaces in the first plate and the second plate for microaligning said plates by mating the depressions of one plate to the projections of the other plate.

17. A method of forming a microchannel device, comprising the steps of:
    (a) providing a first polymeric or ceramic substrate having a substantially planar surface and a second polymeric or ceramic substrate having a substantially planar surface;
    (b) by laser ablation forming a microchannel in the planer surface of the first polymeric or ceramic substrate substantially parallel to said planar surface and forming a microchannel in the planar surface of the second polymeric or ceramic substrate substantially parallel to that planar surface and being a mirror image of the microchannel of the first polymeric or ceramic substrate;
    (c) in a molding process deriving a first plate using the first substrate as a template and deriving a second plate from the second substrate using the second substrate as a template, the first plate having a planar surface and a microchannel corresponding to the planar surface and the microchannel of the first substrate and the second plate having a planar surface and a microchannel corresponding to the planar surface and the microchannel of the second substrate;
    (d) in at least one of the first plate and the second plate providing a plurality of apertures in fluid communication with the microchannel and traversing through the thickness of said at least one plate, permitting the passage of fluid from the microchannel through the thickness of said at least one plate; and (e) aligning the first plate and the second plate such that the microchannel of the second plate is aligned with the microchannel of the first plate in facing abutment, thereby providing a miniaturized column device with a microcompartment including a microchannel.

18. A method of forming a microchannel device, comprising the steps of:

(a) providing a first substrate having a substantially planar surface and a second substrate having a substantially planar surface;

(b) by a "LIGA process" forming a microchannel in the planer surface of the first substrate substantially parallel to said planar surface and forming a microchannel in the planar surface of the second substrate substantially parallel to that planar surface and being a mirror image of the microchannel of the first substrate;

(c) in a molding process deriving a first plate using the first substrate as a template and deriving a second plate from the second substrate using the second substrate as a template, the first plate having a planar surface and a microchannel corresponding to the planar surface and the microchannel of the first substrate and the second plate having a planar surface and a microchannel corresponding to the planar surface and the microchannel of the second substrate;

(d) in at least one of the first plate and the second plate providing a plurality of apertures in fluid communication with the microchannel and traversing through the thickness of said at least one plate, permitting the passage of fluid from the microchannel through the thickness of said at least one plate; and (e) aligning the first plate and the second plate such that the microchannel of the second plate is aligned with the microchannel of the first plate in facing abutment, thereby providing a miniaturized column device with a microcompartment including a microchannel.

19. A method of forming a microchannel device, comprising the steps of:

(a) providing a first polymeric substrate having a substantially planar surface and a second polymeric substrate having a substantially planar surface; and (b) by laser ablation forming a microchannel in the planer surface of the first polymeric substrate substantially parallel to that planar surface and forming a microchannel in the planar surface of the second polymeric substrate substantially parallel to said planar surface and being a mirror image of the microchannel of the first polymeric substrate;

such that when the planar surface of first substrate and the planar surface of the second substrate are aligned in facing abutment the microchannel of the first polymeric substrate is aligned to face the microchannel of the second polymeric substrate to form a microcompartment having an elongated part.

* * * * *